United States Patent
Fuse

(10) Patent No.: US 11,540,809 B2
(45) Date of Patent: Jan. 3, 2023

(54) ULTRASONIC DIAGNOSTIC APPARATUS AND METHOD FOR PROPAGATION SPEED ANALYSIS OF SHEAR WAVE AND ELASTIC MODULUS MEASUREMENT OF A TISSUE

(71) Applicant: Konica Minolta, Inc., Tokyo (JP)

(72) Inventor: Masaru Fuse, Ibaraki (JP)

(73) Assignee: KONICA MINOLTA, INC., Tokyo (JP)

(*) Notice: Subject to any disclaimer, the term of this patent is extended or adjusted under 35 U.S.C. 154(b) by 10 days.

(21) Appl. No.: 16/896,816

(22) Filed: Jun. 9, 2020

(65) Prior Publication Data

US 2021/0007712 A1     Jan. 14, 2021

(30) Foreign Application Priority Data

Jul. 12, 2019    (JP) .............................. JP2019-130047

(51) Int. Cl.
    *A61B 8/08*          (2006.01)
    *A61B 8/00*          (2006.01)
    *A61B 8/15*          (2006.01)

(52) U.S. Cl.
    CPC ................ *A61B 8/485* (2013.01); *A61B 8/15* (2013.01); *A61B 8/4444* (2013.01); *A61B 8/461* (2013.01)

(58) Field of Classification Search
    CPC ......... A61B 8/485; A61B 8/15; A61B 8/4444; A61B 8/461; A61B 8/469; G01S 7/52042
    See application file for complete search history.

(56) References Cited

U.S. PATENT DOCUMENTS 9,339,256 B2 *   5/2016   Specht ................ G01S 15/8922
10,722,215 B2 *   7/2020   Toji ...................... A61B 8/5207
(Continued)

FOREIGN PATENT DOCUMENTS

CN       103462643 A * 12/2013 ............. A61B 8/485
JP        2016049253 A * 4/2016
(Continued)

OTHER PUBLICATIONS

JP-2016049253-A translated (Year: 2016).*
(Continued)

*Primary Examiner* — Joel Lamprecht
*Assistant Examiner* — Nyrobi Celestine
(74) *Attorney, Agent, or Firm* — Lucas & Mercanti, LLP

(57) ABSTRACT

An ultrasonic diagnostic apparatus includes: a hardware processor that determines a focal position of a push wave, and positions of observation points in a region of interest indicating an analysis target range within the subject, causes the ultrasonic probe to perform transmission of a push wave focusing on the focal position, and subsequent to the transmission, causes the ultrasonic probe to transmit a detection wave passing through the region of interest within the subject, and calculates amounts of displacement of tissue of the subject at the observation points on the basis of a reflected wave obtained by the ultrasonic probe in response to the transmission of the detection wave, calculates propagation speeds of the shear wave in the tissue of the subject with respect to the observation points on the basis of the amounts of displacement, and evaluates values of the propagation speeds calculated to create an evaluation result.

12 Claims, 24 Drawing Sheets

(56) References Cited

U.S. PATENT DOCUMENTS

| | | | | |
|---|---|---|---|---|
| 2015/0073275 A1* | 3/2015 | Kanayama | ............ | A61B 8/5223 |
| | | | | 600/443 |
| 2015/0080730 A1* | 3/2015 | Kanayama | ............ | G06T 7/0012 |
| | | | | 600/447 |
| 2015/0119712 A1* | 4/2015 | Tanigawa | ............ | G01S 7/52085 |
| | | | | 600/438 |
| 2015/0164476 A1* | 6/2015 | Kong | .................. | G01S 7/52022 |
| | | | | 600/438 |
| 2015/0164480 A1* | 6/2015 | Watanabe | ............ | A61B 8/5246 |
| | | | | 600/440 |
| 2016/0245905 A1* | 8/2016 | Watanabe | ............ | G01S 7/52049 |
| 2017/0112471 A1* | 4/2017 | Toji | ...................... | A61B 8/4254 |
| 2017/0347990 A1* | 12/2017 | Watanabe | ............ | G01S 7/52022 |
| 2018/0132831 A1* | 5/2018 | Yang | ........................ | A61B 8/54 |
| 2018/0296190 A1* | 10/2018 | Susumu | .................. | G16H 50/30 |
| 2019/0314002 A1* | 10/2019 | Peterson | .................. | A61B 8/14 |
| 2019/0350559 A1* | 11/2019 | Bini | .................... | G01S 7/52022 |
| 2020/0060653 A1* | 2/2020 | Kong | .................. | A61B 8/5207 |

FOREIGN PATENT DOCUMENTS

| | | | | | |
|---|---|---|---|---|---|
| JP | | 2017123994 A | * | 7/2017 | ......... G01S 15/8927 |
| JP | | 2018-038522 A | | 3/2018 | |
| JP | | 2019111104 A | * | 7/2019 | |

OTHER PUBLICATIONS

JP-2017123994-A translated (Year: 2017).*
JP-2019111104-A translated (Year: 2019).*
CN-103462643-A (Year: 2013).*

* cited by examiner

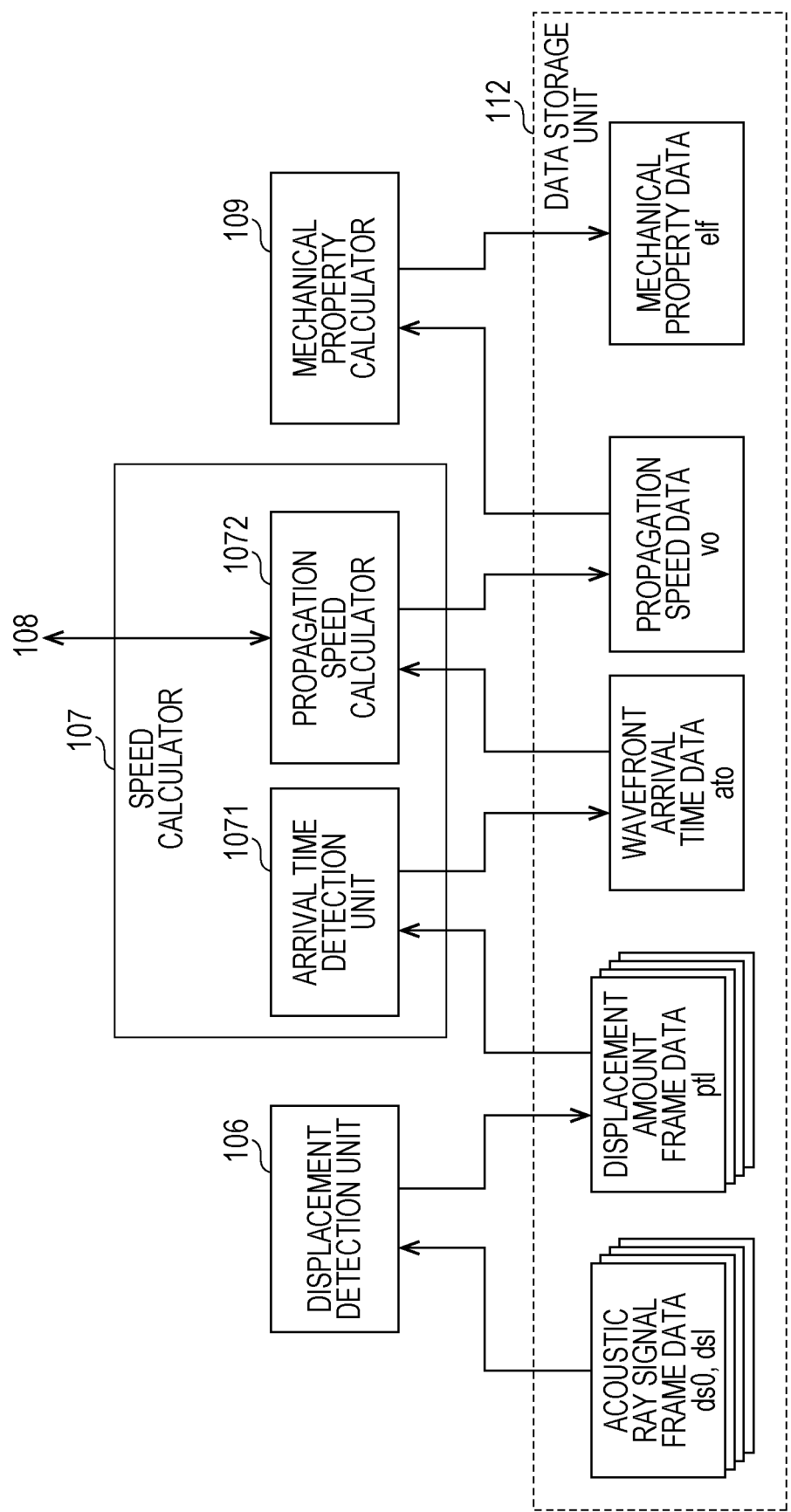

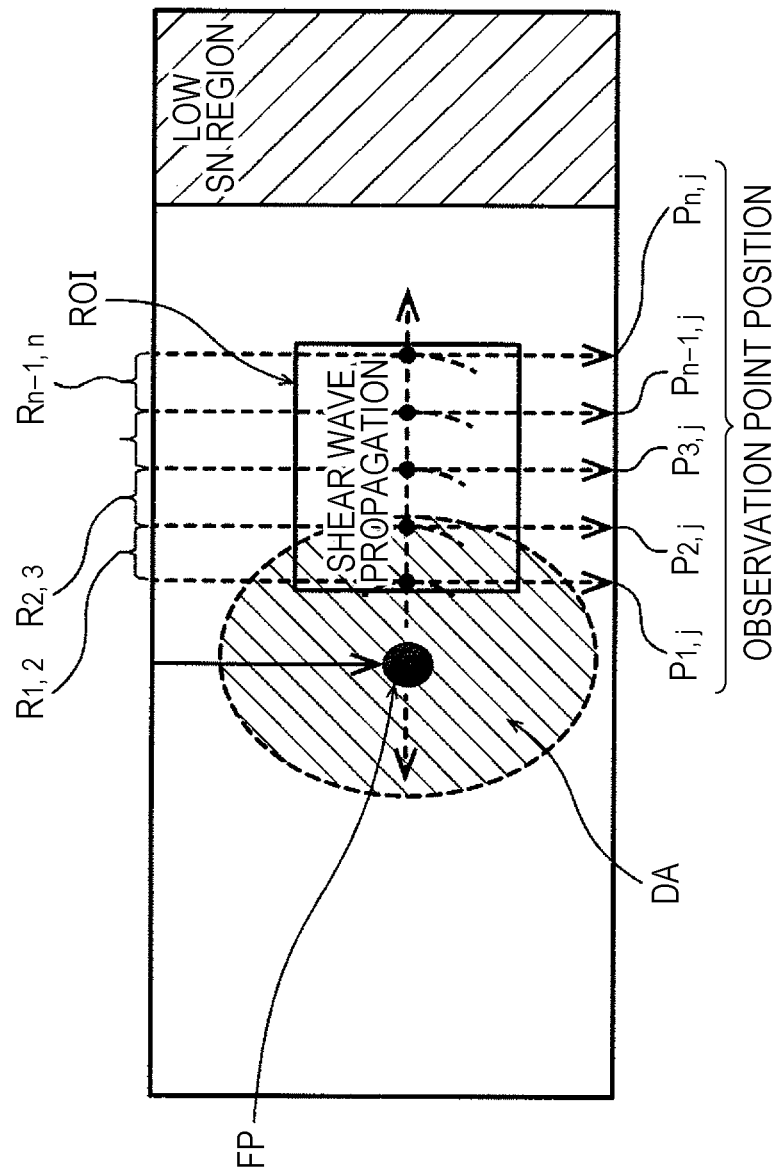

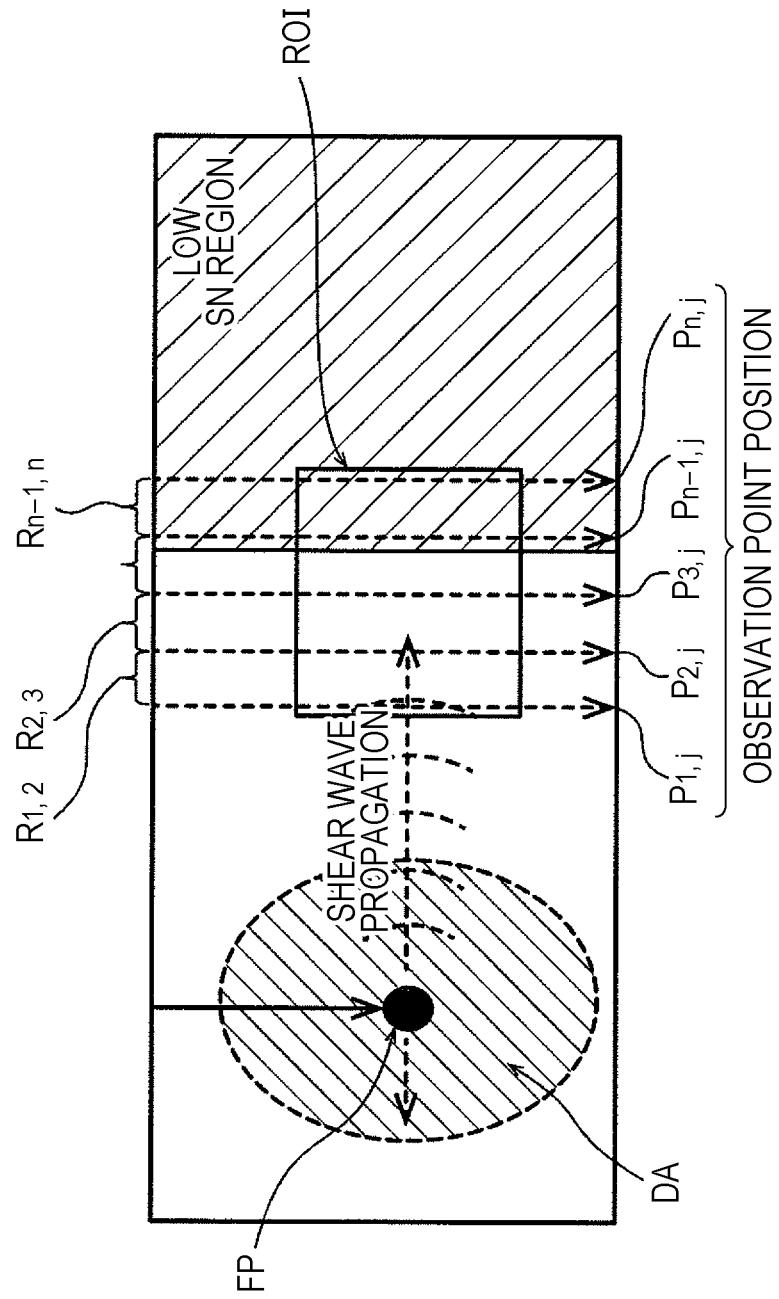

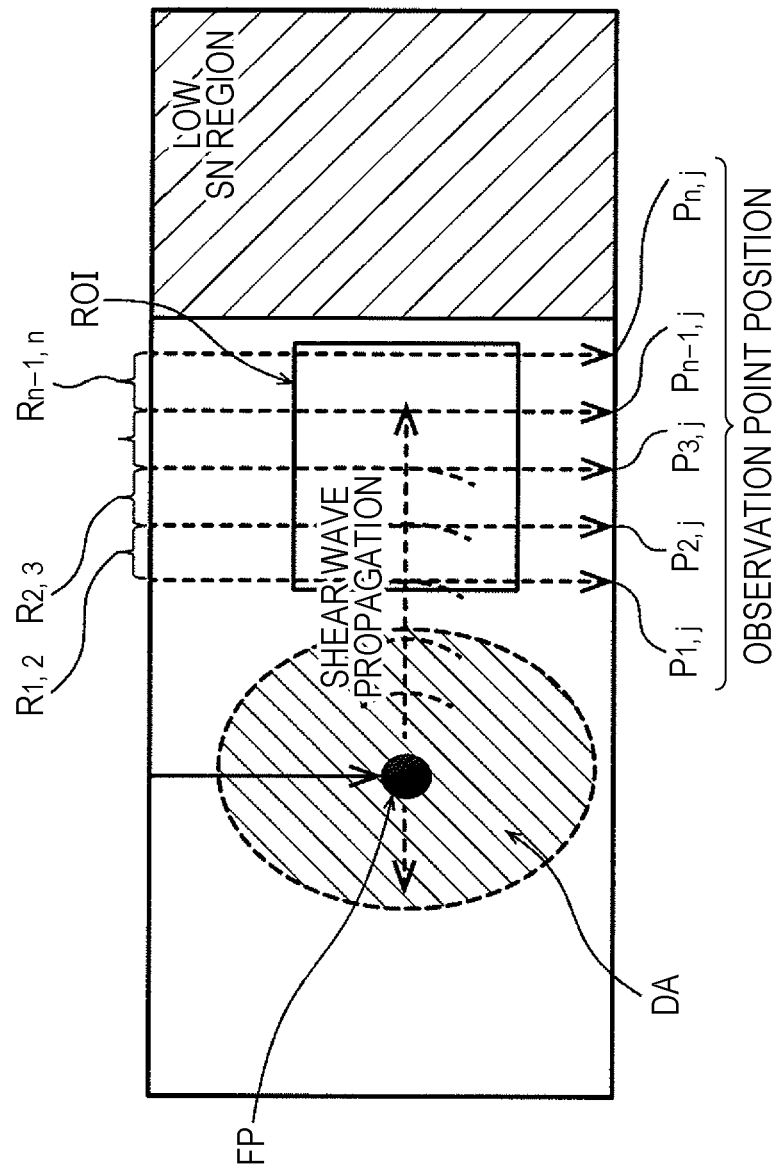

ULTRASONIC DIAGNOSTIC APPARATUS AND METHOD FOR PROPAGATION SPEED ANALYSIS OF SHEAR WAVE AND ELASTIC MODULUS MEASUREMENT OF A TISSUE

The entire disclosure of Japanese patent Application No. 2019-130047, filed on Jul. 12, 2019, is incorporated herein by reference in its entirety.

BACKGROUND

Technological Field

The present disclosure relates to an ultrasonic diagnostic apparatus and a method for controlling the ultrasonic diagnostic apparatus, and more particularly, to a propagation speed analysis of a shear wave in tissue using a shear wave, and an elastic modulus measurement of the tissue.

Description of the Related Art

An ultrasonic diagnostic apparatus is a medical examination apparatus that transmits ultrasonic waves from a plurality of transducers constituting an ultrasonic probe to the inside of a subject, receives ultrasonic reflected waves (echoes) generated by differences in acoustic impedance of the subject tissue, and generates and displays an ultrasonic tomographic image indicating the structure of the internal tissue of the subject on the basis of an obtained electric signal.

In recent years, elastic modulus measurement (Shear Wave Speed Measurement (SWSM), hereinafter referred to as "ultrasonic elastic modulus measurement") of the tissue to which the ultrasonic diagnostic technology is applied has been widely used for examination Since hardness of a tumor found in an organ or body tissue can be measured non-invasively and easily, the ultrasonic elastic modulus measurement can be used for examining hardness of a tumor in cancer screening tests, and evaluation of liver fibrogenesis in liver disease tests, and is useful.

In the ultrasonic elastic modulus measurement, a push wave (focused ultrasound, or Acoustic Radiation Force Impulse (ARFI)) in which ultrasonic waves are focused is transmitted from a plurality of transducers to a specific part within the subject, and then transmission of ultrasonic waves for detection (hereinafter referred to as "detection waves") and reception of reflected waves are repeated multiple times, to perform propagation analysis of a shear wave generated by acoustic radiation pressure of the push wave, whereby a propagation speed of the shear wave can be calculated that represents an elastic modulus of the tissue (for example, JP-A-2018-38522).

In recent years, a "point type" ultrasonic elasticity measurement has been focused that reduces a calculation load by setting a narrow region of interest and measuring a mechanical property such as the elastic modulus of the tissue in the region of interest as a numerical value, and improves accuracy of a calculated absolute value of the mechanical property of the tissue. In the "point type" ultrasonic elasticity measurement, a method is adopted in which a displacement in a direction orthogonal to a propagation direction of the shear wave is detected at a plurality of positions within the subject, and time-series movement of a displacement peak position is detected as movement of the wavefront of the shear wave. The method is characterized in that it has a less calculation load and a higher accuracy of the calculated absolute value of the mechanical property than those of a map type ultrasonic elasticity measurement that analyzes a spatial distribution of the mechanical property in a wide region of interest on the basis of a spatial distribution of the displacement within the subject.

However, there is a variation in signal quality of acoustic ray signals based on the reflected ultrasonic waves of the detection wave depending on a position to be measured within the subject, and there has been a problem that accuracy of detecting the displacement varies depending on the position to be measured.

SUMMARY

The present disclosure has been made in view of the above problem, and it is an object to improve reliability of the absolute value of a measurement result of the mechanical property by improving the accuracy of detecting an amount of displacement, in the ultrasonic elastic modulus measurement that obtains the absolute value of the mechanical property of the tissue from the narrow region of interest.

To achieve the abovementioned object, according to an aspect of the present invention, there is provided an ultrasonic diagnostic apparatus that calculates a propagation speed of a shear wave by exciting the shear wave within a subject by using an ultrasonic probe, and the ultrasonic diagnostic apparatus reflecting one aspect of the present invention comprises: a hardware processor that determines a focal position of a push wave for generating a displacement within the subject, and positions of a plurality of observation points in a region of interest indicating an analysis target range within the subject, causes the ultrasonic probe to perform transmission of a push wave focusing on the focal position, and subsequent to the transmission, causes the ultrasonic probe to transmit a detection wave passing through the region of interest within the subject, and calculates amounts of displacement of tissue of the subject at the plurality of observation points on the basis of a reflected wave obtained by the ultrasonic probe in response to the transmission of the detection wave, calculates propagation speeds of the shear wave in the tissue of the subject with respect to the plurality of observation points on the basis of the amounts of displacement, and evaluates values of the propagation speeds calculated to create an evaluation result, wherein when the evaluation result does not satisfy a predetermined requirement, the hardware processor determines a new focal position and positions of a new plurality of observation points in which at least one of the focal position or the positions of the plurality of observation points is changed on the basis of the evaluation result, and for the new focal position and the positions of the new plurality of observation points determined, calculates the amounts of displacement, calculates the propagation speeds, and evaluates values of the propagation speeds newly calculated to create an evaluation result, and when the evaluation result satisfies the requirement, calculates a propagation speed value in the region of interest on the basis of the propagation speeds with respect to the plurality of observation points.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 8 is a functional block diagram illustrating a configuration of a speed calculator and a mechanical property calculator;

FIGS. 12A to 12C are schematic diagrams each illustrating a positional relationship between the region of interest roi, the push wave focal point FP, and the observation points Pij in operation of the ultrasonic diagnostic apparatus;

DETAILED DESCRIPTION OF EMBODIMENTS

Figure 1:
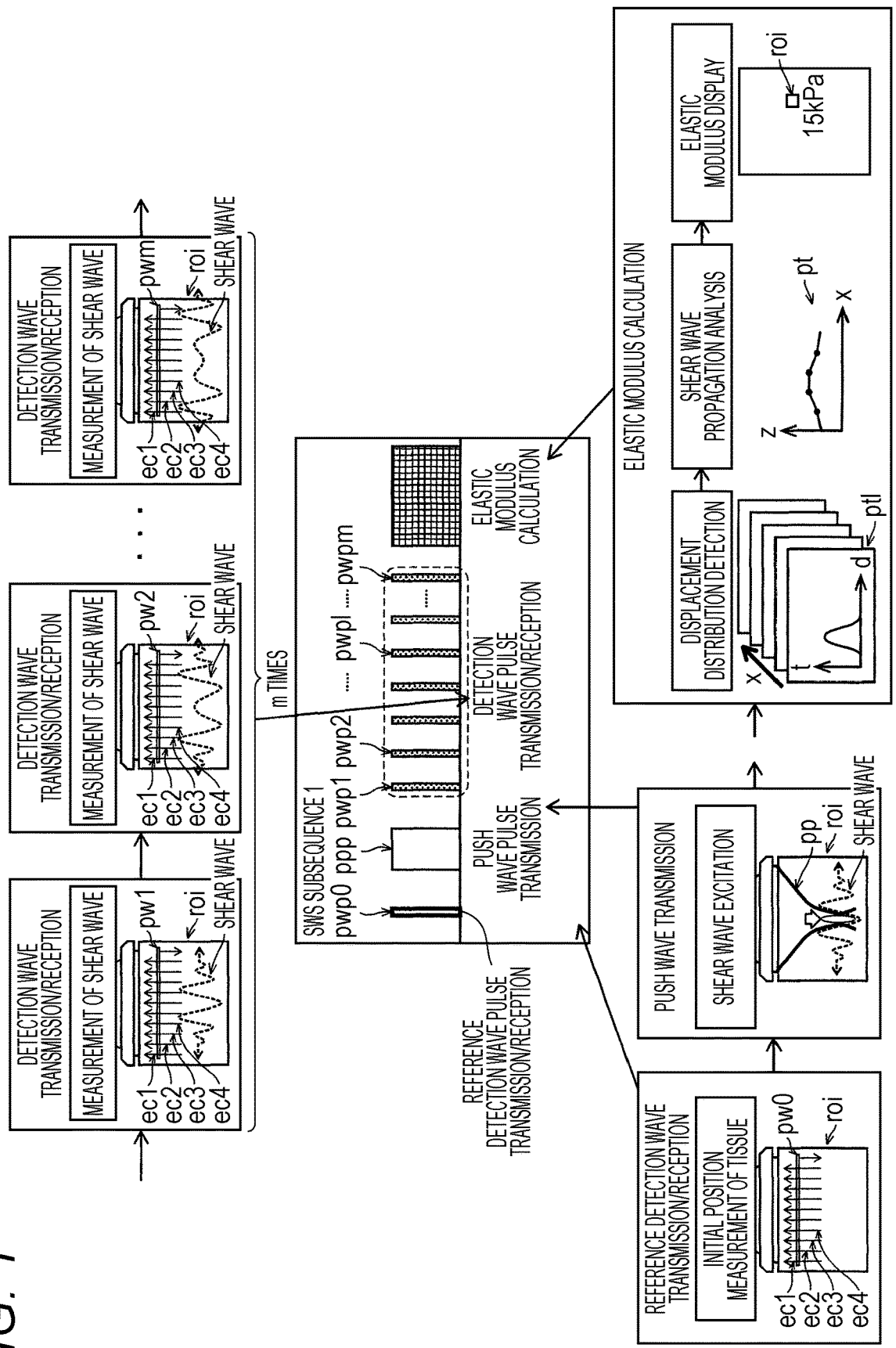
FIG. 1 is a schematic diagram illustrating an outline of an SWS sequence including a shear wave propagation analysis in an ultrasonic diagnostic apparatus according to a first embodiment.

Hereinafter, one or more embodiments of the present invention will be described with reference to the drawings. However, the scope of the invention is not limited to the disclosed embodiments.

<<Circumstances Leading to the Preferred Embodiments>>

The inventor has conducted various studies on improvement of accuracy by control in accordance with calculation capability in ultrasonic elasticity measurement by an ultrasonic diagnostic apparatus. As described above, in the ultrasonic elasticity measurement, a mechanical property is calculated by exciting a shear wave within a subject with a push wave and measuring a propagation speed of the shear wave.

As a method for calculating the propagation speed of the shear wave, there is a so-called "map type" ultrasonic elasticity measurement method in which the wavefront of the shear wave at each time is detected on the basis of a spatial distribution of the displacement within the subject, and a time-series change of a wavefront position of the shear wave is directly analyzed. This method is suitable for analyzing a spatial distribution of the propagation speed in a wide region of interest to obtain a spatial distribution of the mechanical property, or obtain a reliability map of shear wave moving speed based on positions of a shear wave reflection source, refraction source, and the like. On the other hand, there is a problem that the amount of calculation is large since there are many positions of observation points, and the resolution of the moving speed of the shear wave depends on the accuracy of detecting the wavefront, so that a distribution of the mechanical property in the entire region of interest can be grasped but it is difficult to improve the accuracy of the calculated mechanical property.

Thus, in recent years, a so-called "point type" ultrasonic elasticity measurement has been focused that sets a narrow region of interest having a small amount of calculation within the subject and measures the mechanical property of the region of interest as a numerical value. In the "point type" ultrasonic elasticity measurement, a Time to Peak (TTP) method is used in which a narrow region of interest is set within a subject, a plurality of observation points is set in the region, a time is detected when an amount of displacement is maximum (peak) at each observation point (hereinafter, referred to as "peak time"), and the wavefront of the shear wave is regarded as having passed through the observation point at the peak time. Since the shear wave propagates from a focal point of the push wave in a direction substantially orthogonal to a depth direction, in the TTP method, the plurality of observation points is set in the direction substantially orthogonal to the depth direction, and the peak time of the amount of displacement at each observation point is calculated, and a difference Δt in the peak time between the observation points is divided by a distance ΔX between the observation points, whereby a shear wave speed between the observation points is estimated.

The TTP method has a characteristic that the amount of calculation is small and the resolution of the moving speed of the shear wave is high, in particular, in a so-called point type measurement in which the region of interest is narrowed and, for example, an average of the propagation speed of the entire region of interest is calculated, and is suitable for evaluating the absolute value of the mechanical property. On the other hand, the TTP method is easily affected by signal qualities such as a signal level, noise level, and Signal to Noise Ratio (SNR) of an acoustic ray signal based on a reflected detection wave from the observation point due to a change in a measurement position, and the position of the observation point tends to affect reliability of the moving speed of the shear wave.

In such a case, for example, in the "map type" ultrasonic elasticity measurement, an elasticity value of a target is comprehensively (two-dimensionally) obtained, so that appropriate measurement can be performed by performing complementation, correction, and the like on the basis of information of the periphery even if a measurement result at a certain position is incorrect.

However, since the "point type" ultrasonic elasticity measurement is a method of obtaining a highly accurate result by limiting the measurement position, it is difficult to use the information of the peripheral region, and it is necessary to appropriately set the position of the observation point and a transmission position of the push wave so that a shear wave waveform at a target part of the subject and its propagation process can be accurately evaluated.

From the above viewpoint, the inventor has intensively studied a method for improving reliability of the absolute value of the measurement result of the mechanical property by improving the accuracy of detecting the amount of displacement from the observation point in the narrowed region of interest in the point type ultrasonic elasticity measurement having a small amount of calculation.

Then, the inventor has found that in the point type ultrasonic elasticity measurement, the signal quality of the acoustic ray signal based on the reflected detection wave from the observation point and the absolute value of the calculated propagation speed are greatly changed due to a change in the mechanical property of the tissue corresponding to the measurement position, and has conceived that it is necessary to set measurement conditions adapted to the mechanical property of the tissue that is a measurement target to improve the accuracy of detecting the amount of displacement, and has devised an ultrasonic diagnostic apparatus and a method for controlling the ultrasonic diagnostic apparatus according to the present disclosure.

Hereinafter, a detailed description will be given of an ultrasonic diagnostic apparatus and a method for controlling the ultrasonic diagnostic apparatus according to an embodiment, with reference to the drawings.

Embodiment

An ultrasonic diagnostic apparatus 100 performs processing of calculating a propagation speed of a shear wave representing an elastic modulus of tissue by an ultrasonic elastic modulus measurement method. FIG. 1 is a schematic diagram illustrating an outline of an SWS sequence by the ultrasonic elastic modulus measurement method in the ultrasonic diagnostic apparatus 100. As illustrated in the center frame of FIG. 1, the processing of the ultrasonic diagnostic apparatus 100 includes steps of "reference detection wave pulse transmission/reception", "push wave pulse transmission", "detection wave pulse transmission/reception", and "elastic modulus calculation".

In the step of "reference detection wave pulse transmission/reception", a reference detection wave pulse pwp0 is transmitted to an ultrasonic probe, a plurality of transducers is caused to perform transmission of a detection wave pw0 and reception of a reflected wave ec for a range corresponding to a region of interest roi in a subject, and an acoustic ray signal is generated serving as a reference for an initial position of the tissue.

In the step of "push wave pulse transmission", a push wave pulse ppp is transmitted to the ultrasonic probe, the plurality of transducers is caused to transmit a push wave pp in which ultrasonic waves are focused on a specific part within the subject, and a shear wave passing through the region of interest roi is excited.

Thereafter, in the step of "detection wave pulse transmission/reception", a detection wave pulse pwpl is transmitted to the ultrasonic probe, and the plurality of transducers is caused to perform transmission of a detection wave pwl and reception of the reflected wave ec multiple times, whereby a propagation state is measured of the shear wave in the region of interest roi. In the step of "elastic modulus calculation", first, a displacement amount distribution ptl of the tissue due to propagation of the shear wave is calculated in a time series, and then a shear wave propagation analysis is performed that calculates the propagation speed of the shear wave representing the elastic modulus of the tissue from a time-series change of the displacement amount distribution ptl, and finally, the elastic modulus is displayed.

A series of steps involved in one shear wave excitation based on the push wave pp transmission described above is referred to as "Shear Wave Speed (SWS) sequence".

<Ultrasonic Diagnostic System 1000>

(Apparatus Outline)

Figure 2:
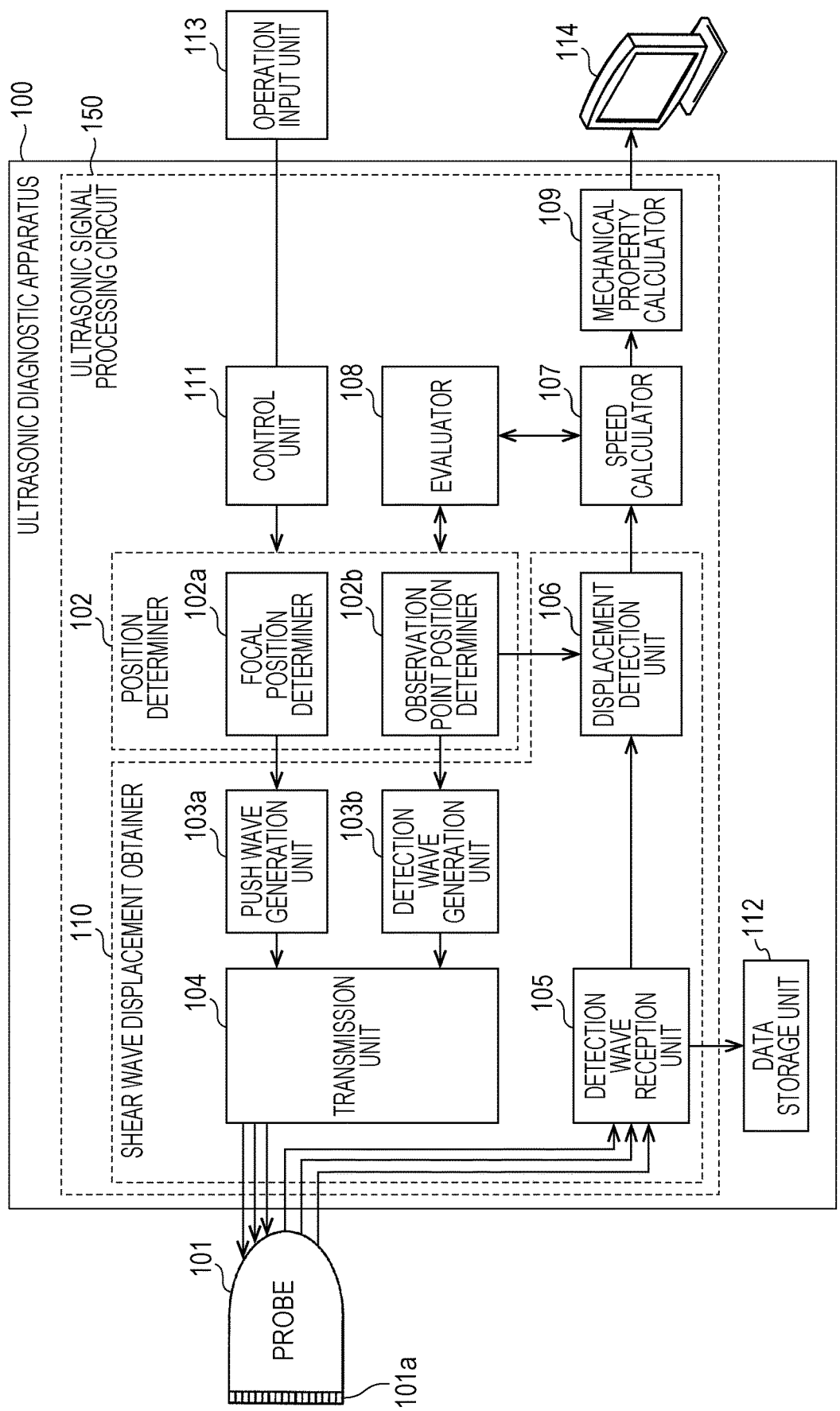
FIG. 2 is a functional block diagram of an ultrasonic diagnostic system including the ultrasonic diagnostic apparatus.

A description will be given of an ultrasonic diagnostic system 1000 including the ultrasonic diagnostic apparatus 100 according to a first embodiment, with reference to the drawings. FIG. 2 is a functional block diagram of the ultrasonic diagnostic system 1000 according to the first embodiment. As illustrated in FIG. 2, the ultrasonic diagnostic system 1000 includes: an ultrasonic probe 101 (hereinafter, referred to as a "probe 101") including a plurality of transducers (transducer row) 101a arranged in a row on the tip surface, the transducers each transmitting an ultrasonic wave toward a subject and receiving a reflected wave of the ultrasonic wave; the ultrasonic diagnostic apparatus 100 that causes the probe 101 to transmit and receive ultrasonic waves and generates an ultrasonic signal on the basis of an output signal from the probe 101; an operation input unit 113 that accepts an operation input from an examiner; and a display unit 114 that displays an ultrasonic image on a screen. The probe 101, the operation input unit 113, and the display unit 114 are each connectable to the ultrasonic diagnostic apparatus 100.

Next, descriptions will be given of elements externally connected to the ultrasonic diagnostic apparatus 100.

(Probe 101)

The probe 101 includes, for example, the transducer row (101a) including the plurality of transducers 101a arranged in a straight line. The probe 101 converts a pulse-like electric signal (hereinafter, referred to as a "transmission signal") supplied from a transmission unit 104 described later into a pulse-like ultrasonic wave. The probe 101 transmits an ultrasonic beam including a plurality of ultrasonic waves emitted from the plurality of transducers to a measurement target in a state in which a transducer surface of the probe 101 is applied to a subject surface with an ultrasonic gel or the like interposed therebetween. Then, the probe 101 receives a plurality of reflected detection waves (hereinafter, referred to as "reflected waves") from the subject, converts these reflected waves into electric signals by the plurality of transducers 101a, respectively, and supplies the electric signals to the ultrasonic diagnostic apparatus 100.

(Operation Input Unit 113)

The operation input unit 113 accepts various operation inputs such as various settings and operations for the ultrasonic diagnostic apparatus 100 from the examiner, and outputs the operation inputs to a control unit 111 of the ultrasonic diagnostic apparatus 100.

The operation input unit 113 may be, for example, a touch panel integrated with the display unit 114. In this case, various settings and operations for the ultrasonic diagnostic apparatus 100 can be performed by performing touch operation or drag operation on operation keys displayed on the display unit 114, and the ultrasonic diagnostic apparatus 100 can be operated by the touch panel. In addition, the operation input unit 113 may be, for example, a keyboard including keys for various operations, an operation panel including buttons and levers for various operations, or a mouse.

<Configuration Outline of Ultrasonic Diagnostic Apparatus 100>

Next, a description will be given of the ultrasonic diagnostic apparatus 100 according to the first embodiment.

The ultrasonic diagnostic apparatus 100 includes: the transmission unit 104 that controls a timing of applying a high voltage to each transducer 101a of the probe 101 to transmit an ultrasonic wave; and a detection wave reception unit 105 that generates an acoustic ray signal by performing reception beam forming on the basis of the reflected waves received by the probe 101.

In addition, the ultrasonic diagnostic apparatus 100 includes: a push wave generation unit 103a that causes the plurality of transducers 101a to transmit the push wave pulse ppp; a detection wave generation unit 103b that causes the detection wave pulse pwpl to be transmitted multiple (m) times subsequent to the push wave pulse ppp; and a position determiner 102 including a push wave focal position determiner 102a and an observation point position determiner 102b.

In addition, the ultrasonic diagnostic apparatus 100 includes: a displacement detection unit 106 that performs a propagation analysis of the shear wave in the region of interest roi on the basis of the acoustic ray signal output by the detection wave reception unit 105; a speed calculator 107 that calculates a propagation speed from the amount of displacement; an evaluator 108 that evaluates a value of the propagation speed; a mechanical property calculator 109 that calculates an elastic modulus from the propagation speed; a data storage unit 112 that stores the acoustic ray signal; and further, the control unit 111 that sets the region of interest roi representing an analysis target range within the subject on the basis of an operation input from the operation input unit 113 and controls each component.

Among the components, the transmission unit 104, the detection wave reception unit 105, the push wave generation unit 103a, the detection wave generation unit 103b, and the displacement detection unit 106 constitute a shear wave displacement obtainer 110. Further, the components of the ultrasonic diagnostic apparatus 100 other than the data storage unit 112 constitute an ultrasonic signal processing circuit 150.

Each component constituting the ultrasonic signal processing circuit 150, for example, the transmission unit 104 and the speed calculator 107 each are implemented by, for example, a hardware circuit such as a Field Programmable Gate Array (FPGA) or an Application Specific Integrated Circuit (ASIC). Alternatively, a configuration may be adopted implemented by a processor such as a Central Processing Unit (CPU) or a Graphics Processing Unit (GPU) and software, and in particular, the configuration using a GPU is referred to as a General-Purpose computing on Graphics Processing Unit (GPGPU). These components can be one circuit part, and can be an assembly of multiple circuit parts. In addition, multiple components can be combined to make one circuit part, and can be an assembly of multiple circuit parts. In addition, the ultrasonic signal processing circuit 150 includes, for example, a GPGPU, and is implemented by a GPU, a memory, a power supply, and software for operating the GPU.

The data storage unit 112 is a computer readable recording medium, and for example, a flexible disk, hard disk, MO, DVD, BD, semiconductor memory can be used. In addition, the data storage unit 112 may be a storage device connected to the ultrasonic diagnostic apparatus 100.

Note that, the ultrasonic diagnostic apparatus 100 according to the embodiment is not limited to the ultrasonic diagnostic apparatus having the configuration illustrated in FIG. 2. For example, a configuration may be adopted in which the transmission unit 104 and the detection wave reception unit 105, or a part thereof are incorporated in the probe 101.

<Configuration of Each Unit of Ultrasonic Diagnostic Apparatus 100>

Next, a description will be given of a configuration of each block included in the ultrasonic diagnostic apparatus 100.

(Control Unit 111)

Generally, in a state in which a B-mode image that is a tomographic image of a subject obtained in real time by the probe 101 is displayed on the display unit 114, an operator designates an analysis target position within the subject and inputs the analysis target position to the operation input unit 113, using the B-mode image displayed on the display unit 114 as an index. The control unit 111 sets the region of interest roi that is the analysis target range, using information designated by the operator from the operation input unit 113 as an input. In the ultrasonic diagnostic apparatus 100, since one value is obtained for the entire region of interest roi as the mechanical property of the subject, the region of interest roi is preferably a narrow range within which the mechanical property does not greatly change. Alternatively, the control unit 111 may set the region of interest roi with a position of the transducer row (101a) including the plurality of transducers 101a in the probe 101 as a reference. For example, the region of interest roi may be set in a front direction of one of the transducers 101a slightly away from the center of the transducer row (101a) including the plurality of transducers 101a.

In addition, the control unit 111 controls other blocks of the ultrasonic diagnostic apparatus 100 described later on the basis of the operation input from the operation input unit 113.

(Push Wave Focal Position Determiner 102a)

The push wave focal position determiner 102a obtains information indicating the region of interest roi from the control unit 111, and sets a transmission focal point FP near the region of interest roi. Specifically, the push wave focal position determiner 102a determines a position of the transmission focal point FP of the push wave on the basis of the information indicating the region of interest roi as described below.

Figure 3A:
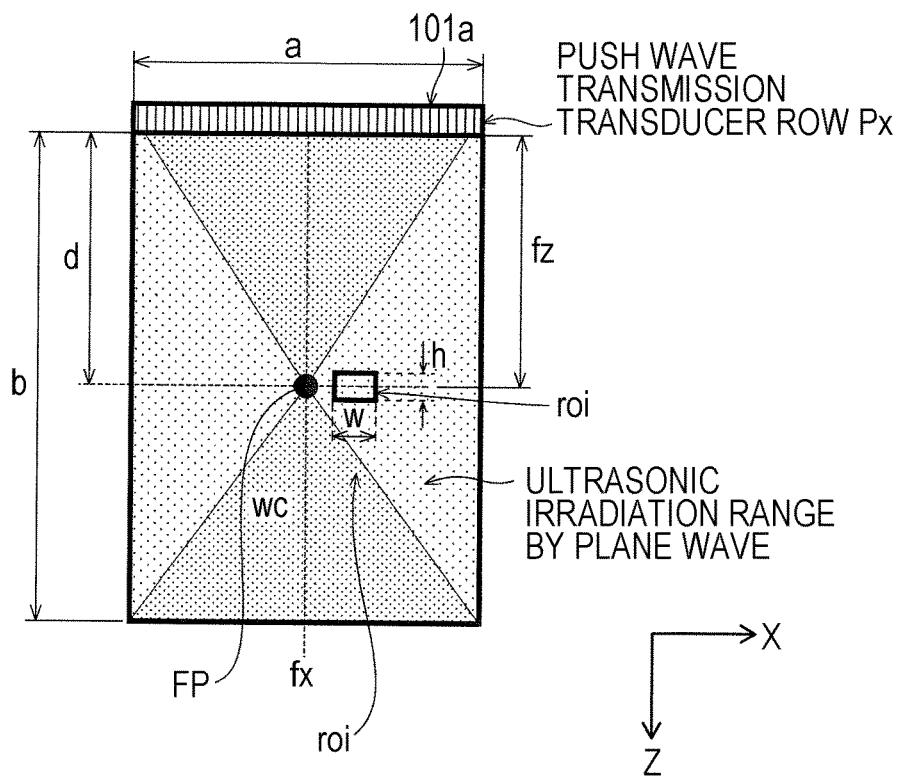
FIG. 3A is a schematic diagram illustrating a position of a transmission focal point FP of a push wave generated by a push wave generation unit.

FIG. 3A is a schematic diagram illustrating the position of the transmission focal point FP of the push wave ppp generated by the push wave generation unit 103a. An example case will be described where a row direction length w and a subject depth direction length h of the region of interest roi are much smaller than a row direction length a and a subject depth direction length b of an ultrasonic irradiation range by a plane wave, respectively, and the region of interest roi is set at the center in the subject depth direction b of the ultrasonic irradiation range, and near the center (a position offset by a predetermined distance from the center) of the row direction length a of the ultrasonic irradiation range.

In the present embodiment, the transmission focal point FP of the push wave is set at the center in the row direction and the depth direction of the ultrasonic irradiation range, and the region of interest roi is set at a position that has the same depth as the transmission focal point FP and is offset by the predetermined distance. Specifically, as illustrated in FIG. 3A, a depth direction transmission focal position fz of the transmission focal point FP is set to coincide with the center of the subject depth direction length b of the ultrasonic irradiation range, and coincide with a depth direction center position of the region of interest roi. In addition, a row direction transmission focal position fx of the transmission focal point FP is set at a position that coincides with the center of the row direction length a of the ultrasonic irradiation range and is offset by the predetermined distance from the region of interest roi. As described above, in the configuration in which the transmission focal point FP is set near the region of interest roi and outside the region of interest roi, the transmission focal point FP is set at a distance at which the shear wave can reach the region of interest roi with respect to the region of interest roi.

Note that, a positional relationship between the region of interest roi and the transmission focal point FP is not limited to the above, and may be changed as appropriate depending on a form or the like of a part to be examined of the subject.

For example, in a case where the region of interest roi is set at a position closer to the center of the row direction length a of the ultrasonic irradiation range, in the example illustrated in FIG. 3A, the row direction transmission focal position fx of the position of the transmission focal point FP may be offset from the center of the row direction length a of the ultrasonic irradiation range, and set at a position offset by the predetermined distance from the region of interest roi. Alternatively, a configuration may be adopted in which the row direction transmission focal position fx of the position of the transmission focal point FP is set inside the region of interest roi. At this time, a configuration may be adopted in which the row direction focal position fx of the transmission focal point FP is offset in the positive or negative direction of the x axis from the row direction center of the region of interest roi and positioned near the boundary of the region of interest roi.

In addition, in the second and subsequent measurements, the push wave focal position determiner 102a may change the position of the transmission focal point FP of the push wave on the basis of an evaluation result of a measurement value of the propagation speed from the evaluator 108. Changing the position of the transmission focal point FP of the push wave will be described later.

(Push Wave Generation Unit 103a)

The push wave generation unit 103a obtains information indicating the position of the transmission focal point FP from the push wave focal position determiner 102a, obtains information indicating the region of interest roi from the control unit 111, and sets a transducer row (hereinafter referred to as a "push wave transmission transducer row Px") caused to transmit the push wave ppp. The push wave transmission transducer row Px is set on the basis of the depth direction transmission focal position fz. In the present embodiment, a configuration is adopted in which a length of the push wave pulse transmission transducer row Px is the length a of the entire row of the plurality of transducers 101a.

Then, the push wave pulse ppp is caused to be transmitted from the transmission unit 104 to the plurality of transducers 101a, whereby the plurality of transducers 101a is caused to transmit the push wave pp in which the ultrasonic beam is focused on a specific part in the subject corresponding to the transmission focal point FR As a result, the shear wave is excited at the specific part in the subject.

Information indicating the position of the transmission focal point FP and the push wave transmission transducer row Px is output to the transmission unit 104 as a transmission control signal together with a pulse width PW and an application start time PT of the push pulse ppp. In addition, a time interval PI of the application start time PT may be included. Note that, the pulse width PW, application start time PT, and time interval PI of the push wave pulse ppp will be described later.

Note that, the ultrasonic beam by the push wave is "focused" means that the ultrasonic beam is narrowed and is a focus beam, that is, an area irradiated with the ultrasonic beam decreases after transmission and takes a minimum value at a specific depth, and is not limited to a case where the ultrasonic beam is focused on one point.

In this case, the "transmission focal point FP" refers to the ultrasonic beam center at a depth at which the ultrasonic beam is focused.

The information indicating the position of the transmission focal point FP and the push wave transmission transducer row Px is output to the transmission unit 104 as the transmission control signal together with the pulse width of the push wave pulse ppp.

(Observation Point Position Determiner 102b)

Figure 9A:
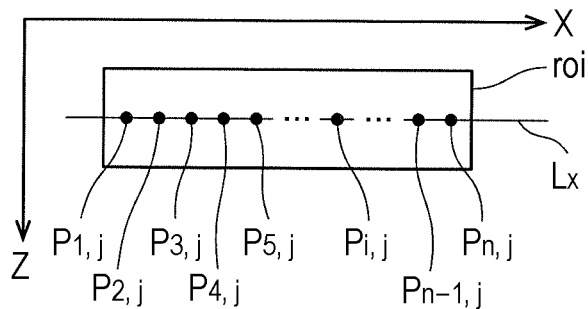
FIG. 9A is a schematic diagram illustrating a relationship between a region of interest roi and observation points Pij.

The observation point position determiner 102b inputs position information of the region of interest roi from the control unit 111, and sets a plurality of observation points corresponding to a measurement position in the region of interest roi. Specifically, as illustrated in FIG. 9A, when the position fz of the push wave transmission focal point FP in the depth direction (Z direction) of the subject and the position of the center of the region of interest roi are the same as each other, a plurality of (n) observation points Pij is set at equal intervals on a straight line Lx passing through the center of the region of interest roi in the Z direction and extending in the row direction (X direction). Thus, an index j indicating the position in the Z direction at the observation point Pij set in the region of interest roi is a fixed value. In addition, the minimum distance between the position fx of the push wave transmission focal point FP in the X direction and the observation point Pij is set to a default initial value. In addition, when the position fz of the push wave transmission focal point FP and the position of the center of the region of interest roi in the Z direction are different from each other, the plurality of observation points Pn1 is set on a straight line passing through the center of the position fz of the push wave transmission focal point FP and parallel to the X direction.

In addition, in the second and subsequent measurements, the observation point position determiner 102b may change the position of the observation point Pij on the basis of the evaluation result of the measurement value of the propagation speed from the evaluator 108. Changing the position of the observation point Pij will be described later.

(Detection Wave Generation Unit 103b)

The detection wave generation unit 103b inputs information indicating the region of interest roi from the control unit 111, and causes the detection wave pulse pwpl to be transmitted multiple times from the transmission unit 104 to the plurality of transducers 101a, thereby causing the plurality of transducers 101a belonging to a detection wave pulse transmission transducer row Tx to transmit a detection wave pw so that the ultrasonic beam passes through the region of interest roi. Specifically, on the basis of the information indicating the region of interest roi, the detection wave generation unit 103b determines a transducer row caused to transmit the detection wave pulse pwpl (hereinafter, referred to as "detection wave transmission transducer row Tx") so that the ultrasonic beam passes through the region of interest roi.

Figure 3B:
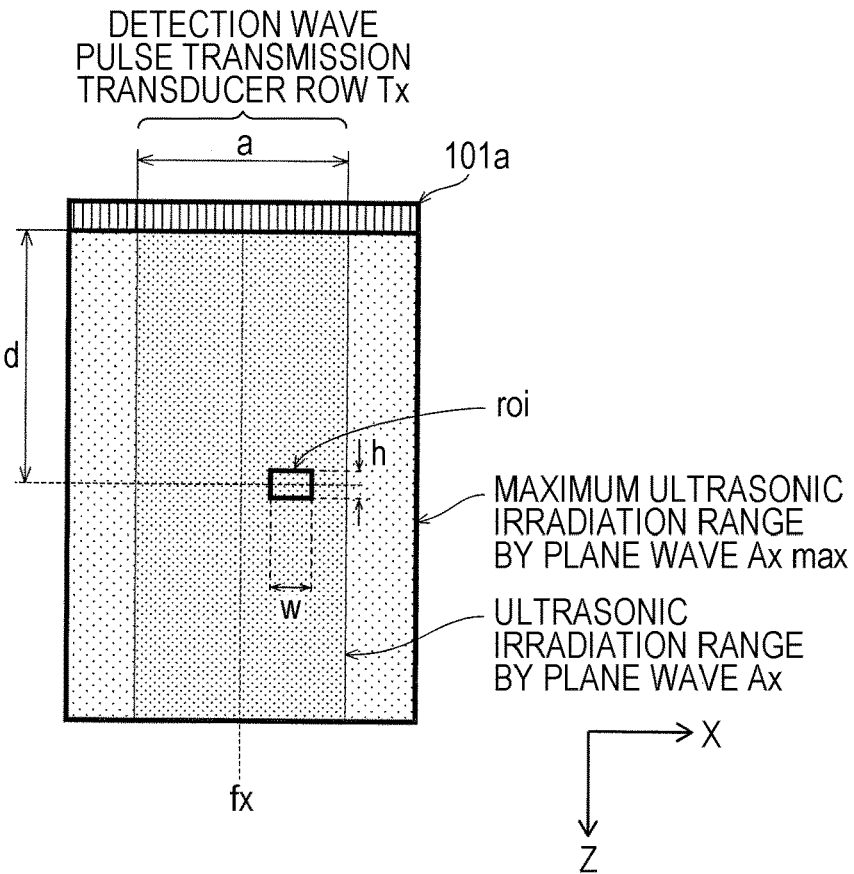
FIG. 3B is a schematic diagram illustrating a configuration outline of a detection wave pulse generated by a detection wave generation unit.

FIG. 3B is a schematic diagram illustrating a configuration outline of the detection wave pulse pwpl generated by the detection wave generation unit 103b. As illustrated in FIG. 3B, the detection wave generation unit 103b sets the detection wave pulse transmission transducer row Tx so that a detection wave passes through the entire region of interest roi, the detection wave being a so-called plane wave in which the detection wave pulse transmission transducer is driven in phase. It is preferable that the length a of the detection wave pulse transmission transducer row Tx is set to be larger than the width w of the region of interest. In this example, the detection wave pulse transmission transducer row Tx is set so that both ends are positioned outside the region of interest roi by a predetermined distance, with the center in the X direction as the row direction transmission focal position fx of the transmission focal point FP. Since the detection wave pw is a plane wave, the detection wave pw propagates in the Z direction perpendicular to the transducer row direction. Thus, the region of interest roi is included in the ultrasonic irradiation region Ax with a margin at both ends in the X direction. As a result, acoustic ray signals can be generated for the observation points in the entire region of interest roi by one transmission and reception of the detection wave, and the detection wave pulse pwpl can be transmitted so that the ultrasonic beam reliably passes through the entire region of interest roi.

Note that, a traveling direction of the ultrasonic beam that is the detection wave is not limited to the Z direction, and may be set so that the ultrasonic beam travels in a direction forming a predetermined azimuth angle θ with respect to the Z direction.

(Transmission Unit 104)

The transmission unit 104 is a circuit that is connected to the probe 101 and controls a timing of applying a high voltage to each of the plurality of transducers included in the push wave transmission transducer row Px or the detection wave transmission transducer row Tx corresponding to all or a part of the plurality of transducers 101a in the probe 101 to transmit ultrasonic waves from the probe 101.

Figure 4A:
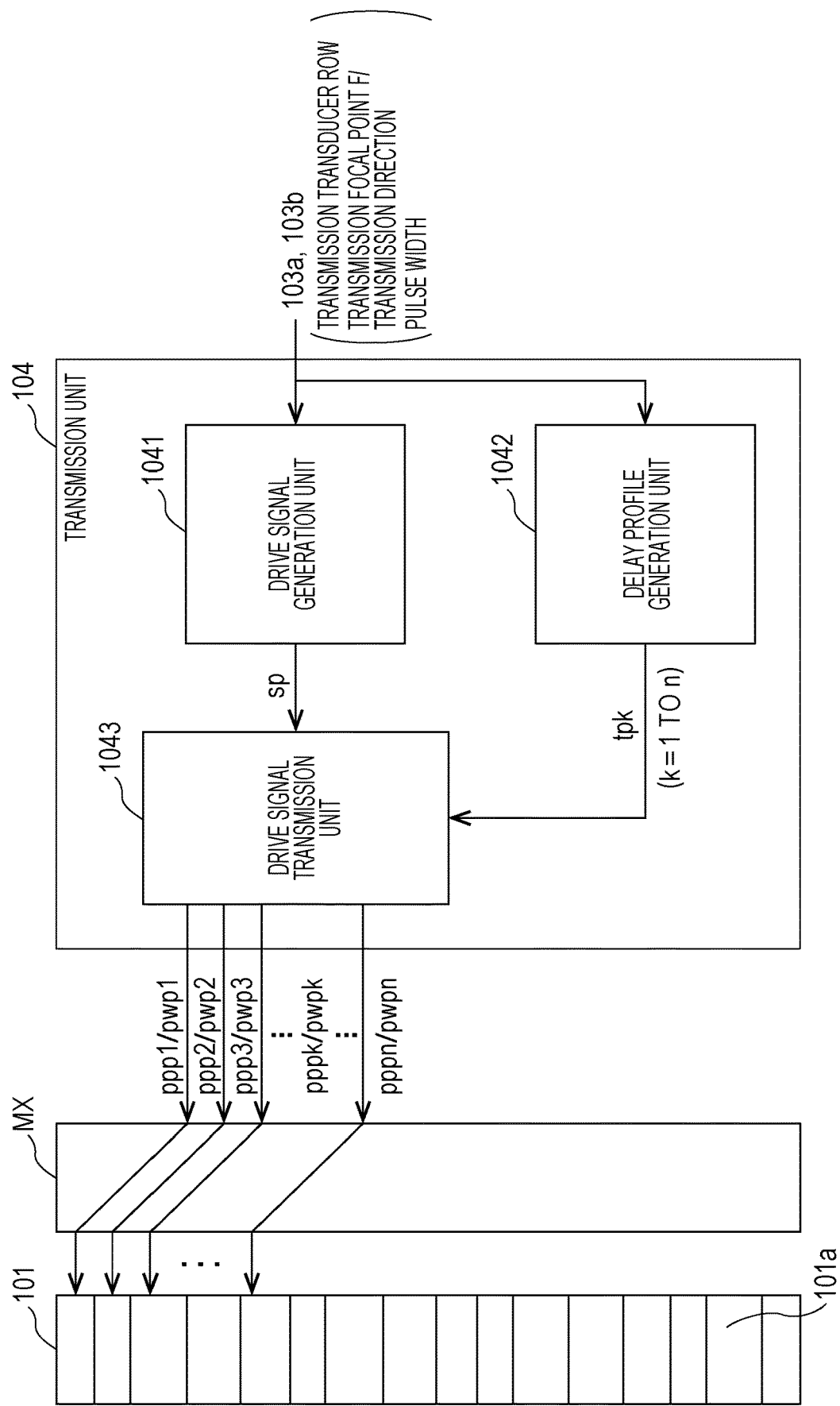
FIG. 4A is a functional block diagram illustrating a configuration of a transmission unit.

FIG. 4A is a functional block diagram illustrating a configuration of the transmission unit 104. As illustrated in FIG. 4A, the transmission unit 104 includes a drive signal generation unit 1041, a delay profile generation unit 1042, and a drive signal transmission unit 1043.

[Drive Signal Generation Unit 1041]

The drive signal generation unit 1041 is a circuit that generates a pulse signal sp for causing an ultrasonic beam to be transmitted from transmission transducers corresponding to a part or all of the transducers 101a in the probe 101 on the basis of each of information indicating the push wave transmission transducer row Px or the detection wave transmission transducer row Tx, information indicating the pulse width PW and the application start time PT of the push wave pulse ppp, and information indicating a pulse width and an application start time of the detection wave pulse pwpl in the transmission control signal from the push wave generation unit 103a or the detection wave generation unit 103b.

[Delay Profile Generation Unit 1042]

The delay profile generation unit 1042 is a circuit that sets and outputs a delay time tppk (k is a natural number from 1 to the number of the transducers 101a, kmax) from the application start time PT that determines a transmission timing of the ultrasonic beam, for each transducer, on the basis of the information indicating the push wave transmission transducer row Px and the position of the transmission focal point FP in the transmission control signal obtained from the push wave generation unit 103a. In addition, the delay profile generation unit 1042 sets and outputs a delay time tpk (k is a natural number from 1 to the number of the transducers 101a, kmax) from the application start time PT that determines a transmission timing of the ultrasonic beam, for each transducer, on the basis of the information indicating the detection wave transmission transducer row Tx in the transmission control signal obtained from the detection wave generation unit 103b. As a result, transmission of the ultrasonic beam is delayed for each transducer by the delay time, and the ultrasonic beam is focused. Note that, the delay time tpk may be set to tpk=0 for all k.

[Drive Signal Transmission Unit 1043]

Figure 5:
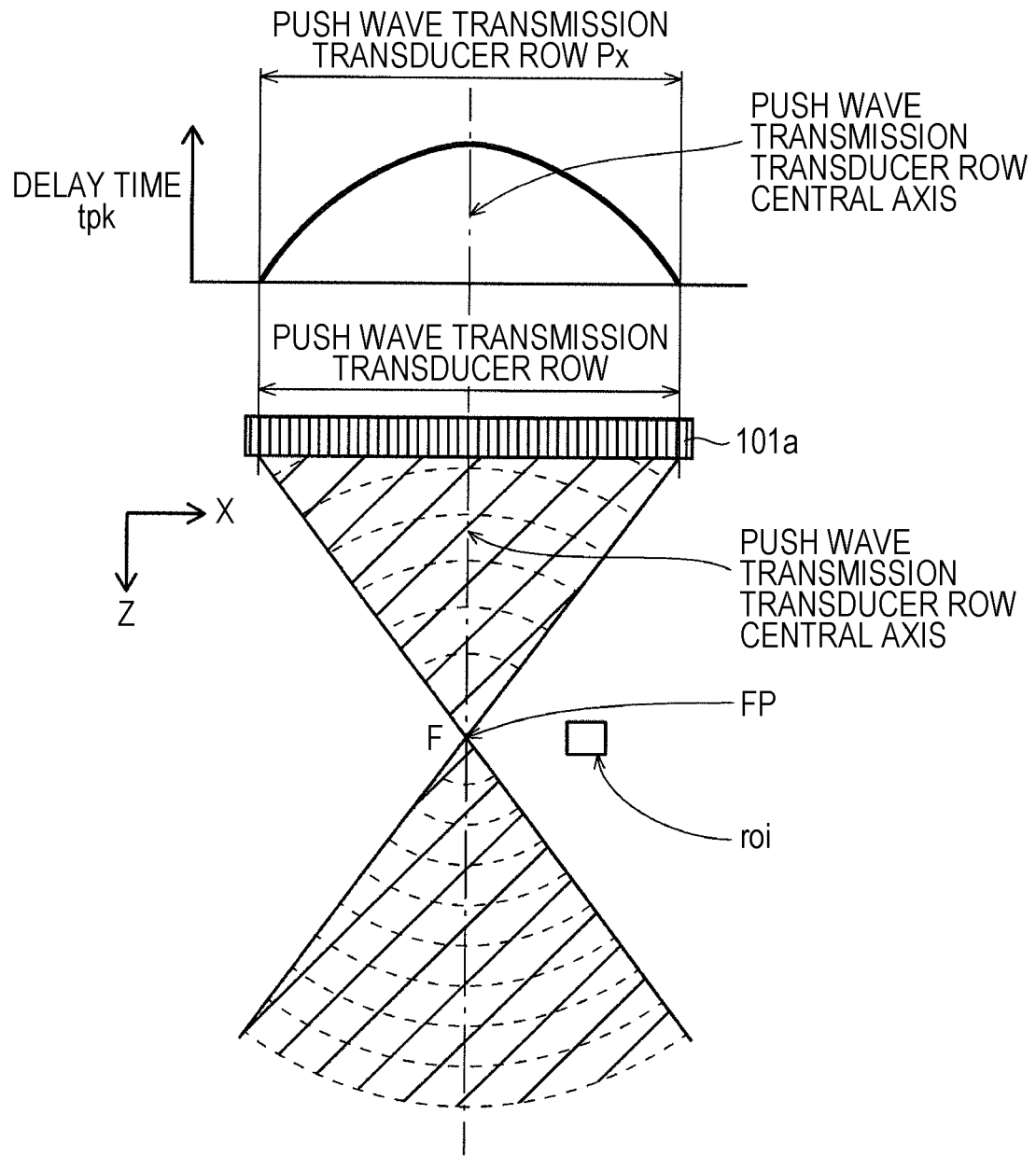
FIG. 5 is a schematic diagram illustrating an outline of the push wave.

The drive signal transmission unit 1043 performs push wave transmission processing that supplies the push wave pulse ppp for causing the push wave to be transmitted from each transducer included in the push wave transmission transducer row Px in the plurality of transducers 101a in the probe 101 as illustrated in the schematic diagram of FIG. 5, on the basis of the pulse signal sp from the drive signal generation unit 1041 and the delay time tpk from the delay profile generation unit 1042. The push wave transmission transducer row Px is determined by the push wave generation unit 103a and selected by a multiplexer MX.

The push wave that causes physical displacement in a living body requires power much larger than that of a transmission pulse used for a normal B-mode display or the like. That is, a drive voltage to be applied to a pulser (ultrasonic generator) may be normally set to 30 to 40 V in obtaining of a B-mode image, whereas the push wave requires, for example, greater than or equal to 50 V. In addition, in the obtaining of the B-mode image, a transmission pulse length is about several μsec, but the push wave may require a transmission pulse length of several hundred μsec per transmission.

Figure 6A:
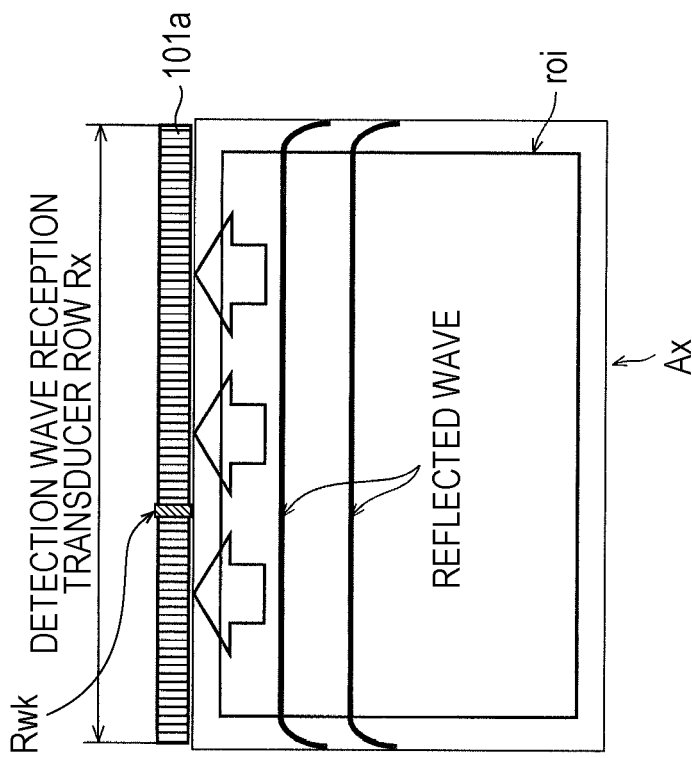
FIG. 6A is a schematic diagram illustrating an outline of detection wave transmission.

In the present embodiment, as illustrated in the schematic diagram of FIG. 6A, the push wave pulse ppp is transmitted from the drive signal transmission unit 1043 to the plurality of transducers 101a at the application start time PT. The push wave pulse ppp includes a burst signal having the predetermined pulse width PW (time length), a predetermined voltage amplitude (+V to −V), and a predetermined frequency. Specifically, the pulse width PW may be, for example, 100 to 200 μsec, the frequency may be, for example, 6 MHz, and the voltage amplitude may be, for example, +50 V to −50 V. However, it goes without saying that the application conditions are not limited to the above.

In addition, the drive signal transmission unit 1043 performs wave transmission processing that supplies the detection wave pulse pwpl for causing the ultrasonic beam to be transmitted from each transducer included in the detection wave transmission transducer row Tx in the plurality of transducers 101a in the probe 101. The detection wave transmission transducer row Tx is determined by the detection wave generation unit 103b and selected by the multiplexer MX. For example, a configuration may be adopted in which the multiplexer MX is not used.

After transmitting the push wave pulse ppp, the transmission unit 104 transmits the detection wave pulse pwpl multiple times on the basis of the transmission control signal from the detection wave generation unit 103b. Each of a series of detection wave pulse pwpl transmissions performed multiple times from the same detection wave transmission transducer row Tx after one push wave pulse ppp transmission is referred to as a "transmission event".

(Detection Wave Reception Unit 105)

The detection wave reception unit 105 is a circuit that generates acoustic ray signals for the plurality of observation points Pij existing within the region of interest roi and generates a sequence of acoustic ray signal frame data dsl (l is a natural number from 1 to m, and when numbers are not distinguished, acoustic ray signal frame data dsl) on the basis of the reflected waves from the subject tissue received in a time series by the plurality of transducers 101a corresponding to each of the multiple times of the detection wave pulse pwpl. That is, after transmitting the detection wave pulse pwpl, the detection wave reception unit 105 generates the acoustic ray signals from the electric signals obtained by the plurality of transducers 101a on the basis of the reflected waves received by the probe 101. Here, i is a natural number indicating the order in the X direction at the plurality of observation points Pij in the region of interest roi, and j is a natural number indicating the order in the Z direction. Note that, the "acoustic ray signal" is a signal obtained by performing phasing addition processing on received signals (RF signals).

Figure 4B:
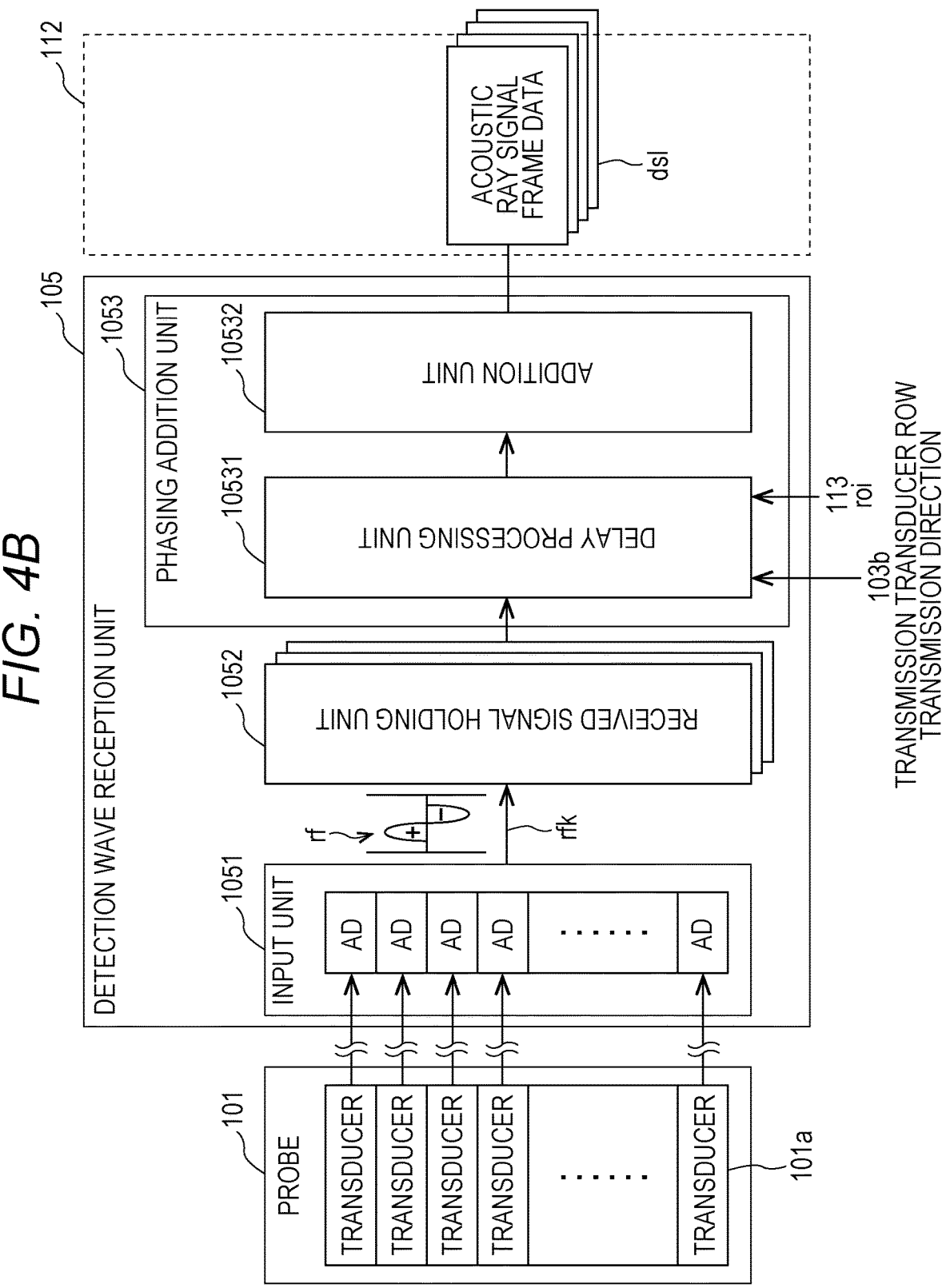
FIG. 4B is a functional block diagram illustrating a configuration of a detection wave reception unit.

FIG. 4B is a functional block diagram illustrating a configuration of the detection wave reception unit 105. The detection wave reception unit 105 includes an input unit 1051, a received signal holding unit 1052, and a phasing addition unit 1053.

[Input Unit 1051]

The input unit 1051 is a circuit that is connected to the probe 101 and generates the received signal (RF signal) on the basis of the reflected wave from the probe 101. Here, a received signal rfk (k is a natural number from 1 to n) is a so-called RF signal obtained by A/D conversion of an electric signal converted from the reflected wave received by each transducer on the basis of the transmission of the detection wave pulse pwpl, and the received signal rfk includes a signal sequence (received signal sequence) that is continuous in a transmission direction (depth direction of the subject) of the ultrasonic wave received by each of reception transducers rwk.

Figure 6B:
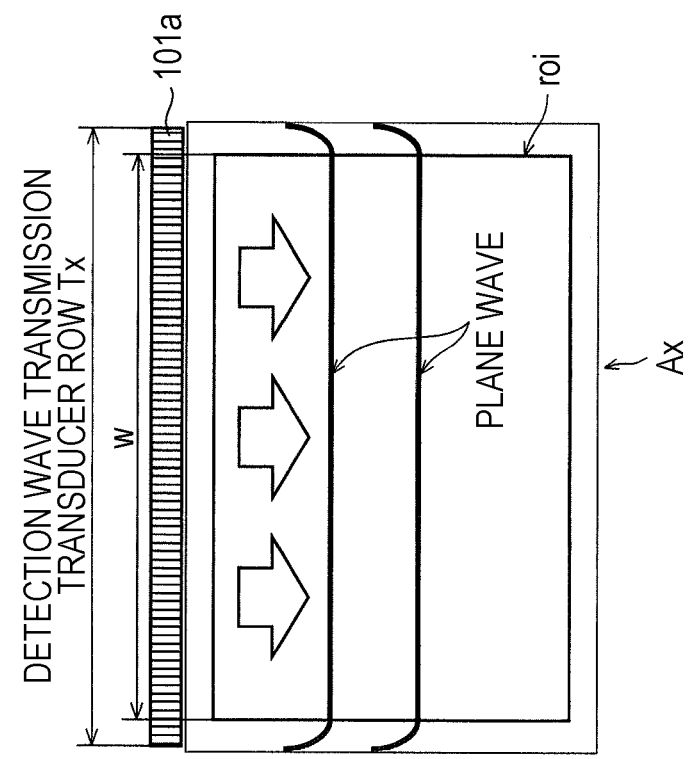
FIG. 6B is a schematic diagram illustrating an outline of reflected wave reception.

The input unit 1051 generates a sequence of the received signal rfk for each reception transducer rwk for each transmission event on the basis of the reflected wave obtained by each of the reception transducers rwk. A wave reception transducer row includes a transducer row corresponding to a part or all of the plurality of transducers 101a in the probe 101, and is selected by the multiplexer MX on the basis of an instruction from the control unit 111. In this example, a configuration is adopted in which all of the plurality of transducers 101a are selected as the reception transducer row. As a result, as illustrated in FIG. 6B illustrating an outline of the reflected detection wave reception, it is possible to receive the reflected waves from the observation points existing in the entire detection wave irradiation region Ax by using all the transducers in one reception processing, and generate a received signal sequence for all transducers. The generated received signal rfk is output to the received signal holding unit 1052.

[Received Signal Holding Unit 1052]

The received signal holding unit 1052 is a computer readable recording medium, and for example, a semiconductor memory or the like can be used. The received signal holding unit 1052 inputs the received signal rfk for each reception transducer rwk from the input unit 1051 in synchronization with the transmission event, and holds the received signal rfk until one acoustic ray signal frame data is generated.

Note that, the received signal holding unit 1052 may be a part of the data storage unit 112.

[Phasing Addition Unit 1053]

The phasing addition unit 1053 is a circuit that generates an acoustic ray signal ds by performing delay processing on the received signal rfk received by a reception transducer Rpk included in a detection wave pulse reception transducer row Rx for each of the observation points Pij within the region of interest roi in synchronization with the transmission event, and then performing addition for all the reception transducers Rpk. Here, as illustrated in FIG. 9A, it is preferable that the observation points Pij are arranged at equal intervals in the row direction (X direction), and the positions in the depth direction (Z direction) are uniform. Specifically, the observation points Pij are arranged at equal intervals in the X direction on a straight line extending in the row direction (X direction). The detection wave pulse reception transducer row Rx includes the reception transducer Rpk corresponding to a part or all of the plurality of transducers 101a in the probe 101, and is selected by the phasing addition unit 1053 and the multiplexer MX on the basis of an instruction from the control unit 111. In this example, as the reflected wave reception transducer row Rx, a transducer row is selected including at least all of the transducers constituting the detection wave pulse transmission transducer row Tx in each transmission event.

The phasing addition unit 1053 includes a delay processing unit 10531 and an addition unit 10532 for performing processing on the received signal rfk.

The delay processing unit 10531 is a circuit that identifies a received signal corresponding to the reception transducer Rpk based on reflected ultrasonic waves from the observation points Pij, from the received signal rfk for the reception transducer Rpk in the detection wave pulse reception transducer row Rx, by performing compensation by an arrival time difference (amount of delay) of the reflected ultrasonic wave to each of the reception transducers Rpk, the arrival time difference being obtained by dividing a difference between the observation point Pij and each of the reception transducers Rpk by the sound speed value.

Figure 7:
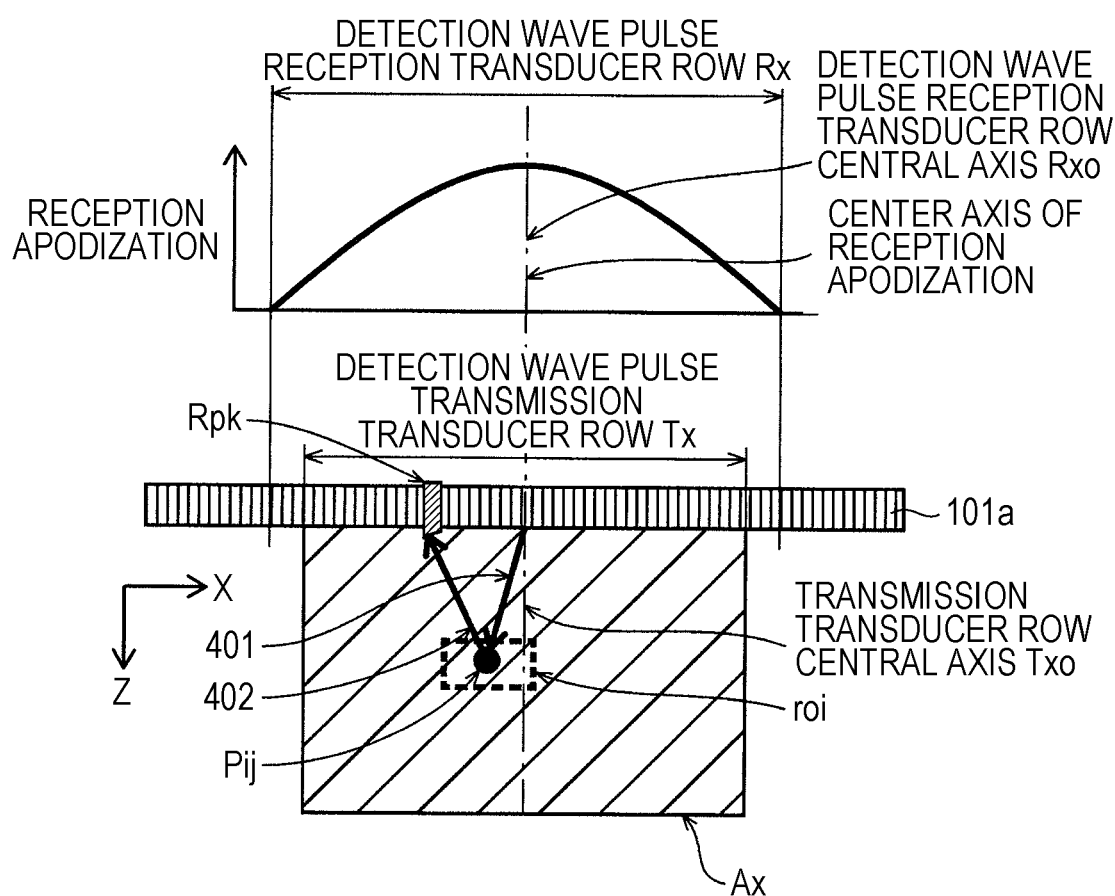
FIG. 7 is a schematic diagram illustrating an outline of a method for calculating a propagation path in an ultrasonic wave in a delay processing unit.

FIG. 7 is a schematic diagram illustrating an outline of a method for calculating a propagation path in an ultrasonic wave in the delay processing unit 10531. FIG. 7 illustrates a propagation path of an ultrasonic wave radiated from the detection wave pulse transmission transducer row Tx, reflected at an observation point Pij at an arbitrary position within the region of interest roi, and reaching the reception transducer Rpk.

The delay processing unit 10531 specifies a transmission path to the observation point Pij in response to the transmission event, and calculates a transmission time by dividing a distance of the transmission path by the sound speed. The transmission path can be, for example, a straight path from the center of the detection wave transmission transducer row Tx to the observation point Pij. Note that, the transmission path is not limited to this, and may be, for example, the shortest path from the center of the detection wave transmission transducer row Tx to an arbitrary point having the same depth as that of the observation point Pij.

In response to the transmission event, for the observation point Pij, the delay processing unit 10531 specifies a reception path that is reflected at the observation point Pij and reaches the reception transducer included in the detection wave reception transducer row, and calculates a reception time by dividing a distance of the reception path by the sound speed. The reception path can be, for example, a straight path from the observation point Pij to the reception transducer.

Next, the delay processing unit 10531 calculates a total propagation time to each reception transducer from the transmission time and the reception time, and calculates the amount of delay to be applied to a received signal sequence rfk for each reception transducer on the basis of the total propagation time.

Next, from the received signal sequence rfk for each reception transducer, the delay processing unit 10531 identifies the received signal rfk corresponding to the amount of delay (received signal corresponding to the time obtained by subtracting the amount of delay) as a signal corresponding to the reception transducer based on the reflected wave from the observation point Pij.

In response to the transmission event, the delay processing unit 10531 identifies the received signal rfk for each reception transducer Rpk for all the observation points Pij positioned within the region of interest roi, using the received signal rfk from the received signal holding unit 1052 as an input.

The addition unit 10532 is a circuit that uses the received signal rfk that is identified correspondingly to the reception transducer Rpk and output from the delay processing unit 10531 as an input, adds them together, and generates an acoustic ray signal dsij to which phasing addition is performed for the observation point Pij.

Further, the acoustic ray signal dsij for the observation point Pij may be generated by multiplying the received signal rfk identified correspondingly to each reception transducer Rpk by a reception apodization (weight sequence) and then performing addition. The reception apodization is a sequence of weighting factors applied to the received signal corresponding to the reception transducer Rpk in the detection wave reception transducer row Rx. The reception apodization is set, for example, so that the weight for the transducer positioned at the center in the row direction of the detection wave reception transducer row Rx is maximized, and a central axis of the distribution of the reception apodization coincides with a detection wave reception transducer row central axis Rxo, and the distribution has a shape symmetric with respect to the central axis. The shape of the distribution is not particularly limited. Note that, the reception apodization is not limited to the above-described case, and may be set, for example, so that the weight for the transducer positioned at the row direction center of the transmission transducer row Tx is maximized.

The addition unit 10532 generates the acoustic ray signal dsij for all the observation points Pij existing within the region of interest roi, and generates the acoustic ray signal frame data dsl.

Then, transmission and reception of the detection wave pulse pwpl are repeated in synchronization with the transmission event, and the acoustic ray signal frame data dsl for all the transmission events is generated. The generated acoustic ray signal frame data dsl is output to the data storage unit 112 for each transmission event and stored.

(Displacement Detection Unit 106)

The displacement detection unit 106 is a circuit that detects the magnitude (amount of displacement) of the displacement of the tissue within the region of interest roi from the sequence of the acoustic ray signal frame data dsl for the observation point Pij.

FIG. 8 is a functional block diagram illustrating a configuration of the displacement detection unit 106, the speed calculator 107, and the mechanical property calculator 109.

The displacement detection unit 106 obtains one frame of the acoustic ray signal frame data dsl included in the sequence of the acoustic ray signal frame data dsl, and acoustic ray signal frame data (reference acoustic ray signal frame data) ds0 serving as a reference, for each of the observation points Pij. The reference acoustic ray signal frame data ds0 is a signal serving as a reference for extracting a displacement due to a shear wave in the acoustic ray signal frame data dsl corresponding to each transmission event, and specifically, is frame data of an acoustic ray signal obtained from the region of interest roi before the transmission of the push wave pulse ppp. The displacement detection unit 106 detects the amount of displacement of each of the observation points Pij from a difference between the acoustic ray signal frame data dsl and the reference acoustic ray signal frame data ds0. Then, the displacement detection unit 106 creates time-series data (displacement signal) of the amount of displacement of each of the observation points Pij by repeating this processing. The displacement detection unit 106 generates displacement amount frame data ptl by associating the time-series data of the amount of displacement with the observation point Pij and the transmission event.

(Speed Calculator 107)

The speed calculator 107 is a circuit that calculates the propagation speed of the shear wave from the amount of displacement calculated.

The speed calculator 107 includes an arrival time detection unit 1071 and a propagation speed calculator 1072.

Figure 9B:
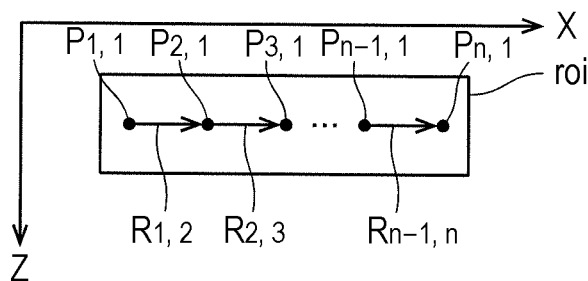
FIGS. 9B to 9D are schematic diagrams illustrating an outline of a propagation analysis in the region of interest roi.
Figure 9C:
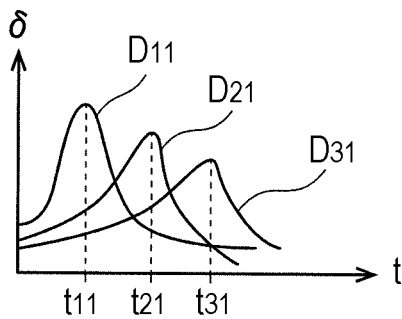

The arrival time detection unit 1071 detects an arrival time of the wavefront of each of the observation points Pij on the basis of the displacement amount frame data ptl. Specifically, as illustrated in FIG. 9C, a peak time tij is detected of an amount of displacement Dij of each of the observation points Pij. Note that, as a method for detecting the peak time tij, a known method can be used, such as a Time to Peak (TTP) method or a correlation processing method.

The arrival time detection unit 1071 generates wavefront arrival time data ato by associating the peak time tij with the observation point Pij.

Figure 9D:
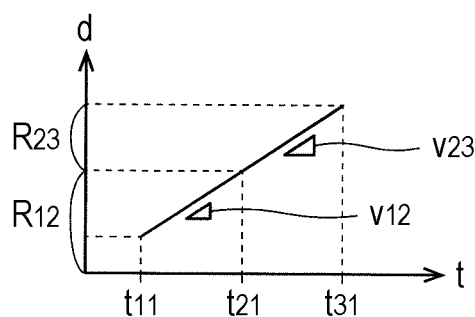

The propagation speed calculator 1072 calculates each of propagation speeds v of the shear wave between adjacent observation points Pij in the region of interest. Specifically, as illustrated in FIGS. 9B and 9D, a distance Ri(i+1) between two adjacent observation points Pij and P(i+1)j is divided by a difference $\{t(i+1)j-tij\}$ between the respective peak times tij and t(i+1)j of the observation points Pij and P(i+1)j, whereby the propagation speed vi(i+1) is calculated. Note that, the d-axis of the vertical axis in FIG. 9D is a distance axis indicating a traveling path of the shear wave.

The propagation speed calculator 1072 outputs to the evaluator 108 the propagation speed in an evaluation target division to be evaluated in the evaluator 108 from the propagation speeds vi(i+1) calculated for the plurality of (n) observation points Pij in the region of interest. In the present embodiment, for example, the propagation speed v12, v23, or vn−1n of a first division (i=1), a second division (i=2), or a final division (i=n−1) is output to the evaluator 108.

In addition, when an evaluation result that the evaluation result of the measurement value of the propagation speed satisfies a requirement (appropriate) is obtained from the evaluator 108, the propagation speed calculator 1072 calculates a representative value of the propagation speeds v of the shear wave as a propagation speed of the shear wave in the region of interest. The representative value includes, for example, an average value and a median value.

The propagation speed calculator 1072 outputs the propagation speed of the shear wave in the region of interest as propagation speed data vo.

(Mechanical Property Calculator 109)

The mechanical property calculator 109 is a circuit that converts the propagation speed into a mechanical property value of the tissue. The mechanical property calculator 109 converts the propagation speed of the shear wave in the region of interest into a mechanical property value of the subject. The mechanical property includes, for example, a shear modulus, Young's modulus, dynamic shear viscosity, mechanical impedance, and the like.

For example, a shear modulus G can be calculated by the following equation using subject density p and the propagation speed v of the shear wave.

$$G = \rho \cdot v^2$$

In addition, for example, a Young's modulus E is expressed as $E=2(1+v)G$ using the Poisson's ratio v when it is assumed that the subject is an isotropic elastic body, so that the Young's modulus E can be calculated by the following equation assuming $v=0.5$.

$$E = 3\rho \cdot v^2$$

Similarly, each of the dynamic shear viscosity and the mechanical impedance can be calculated by a known calculation using the propagation speed v of the shear wave.

The mechanical property calculator 109 outputs the mechanical property value in the region of interest as mechanical property data elf.

(Evaluator 108)

The evaluator 108 is a circuit that obtains the propagation speed from the speed calculator 107 and calculates a signal level and/or a noise level.

Here, a description will be given of an object of measuring the propagation speed, the amount of displacement, or the signal level and signal to noise ratio of the acoustic ray signal (hereinafter referred to as "measurement quality") in the evaluator 108.

Figure 10A:
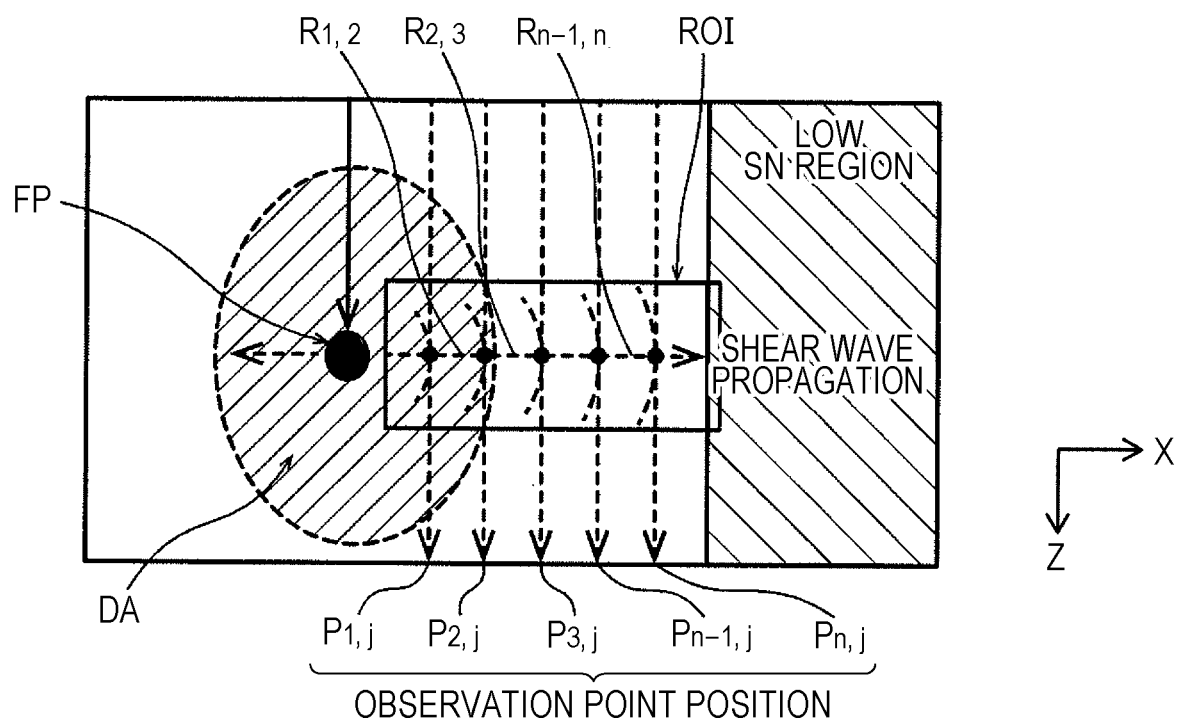
FIG. 10A is a schematic diagram illustrating an example of operation of a propagation analysis of a shear wave.
Figure 10B:
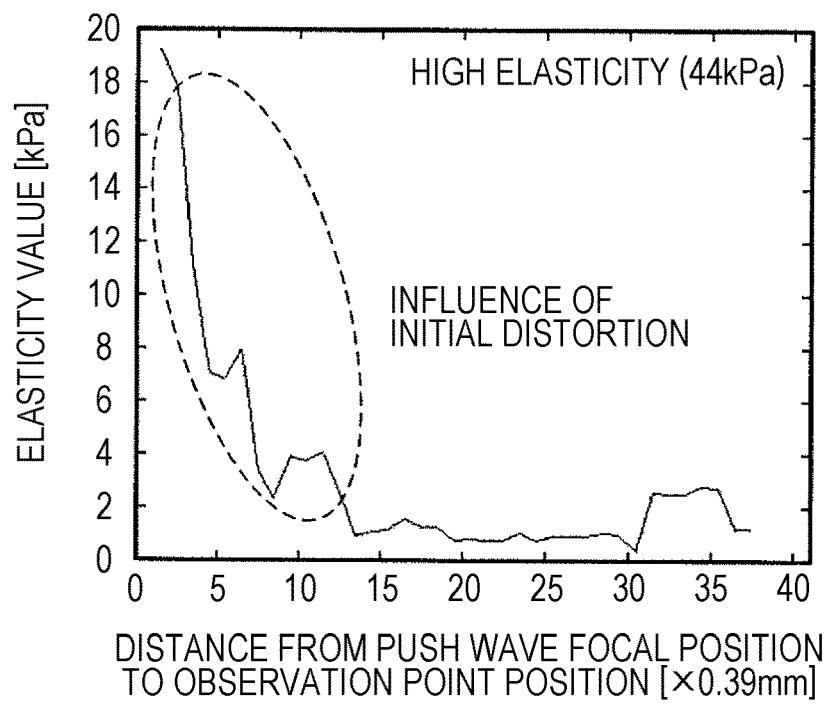
FIG. 10B is a diagram illustrating an experimental result illustrating a relationship between a distance from a push wave focal position FP to a position of the observation point Pij and a measured elasticity value.
Figure 10C:
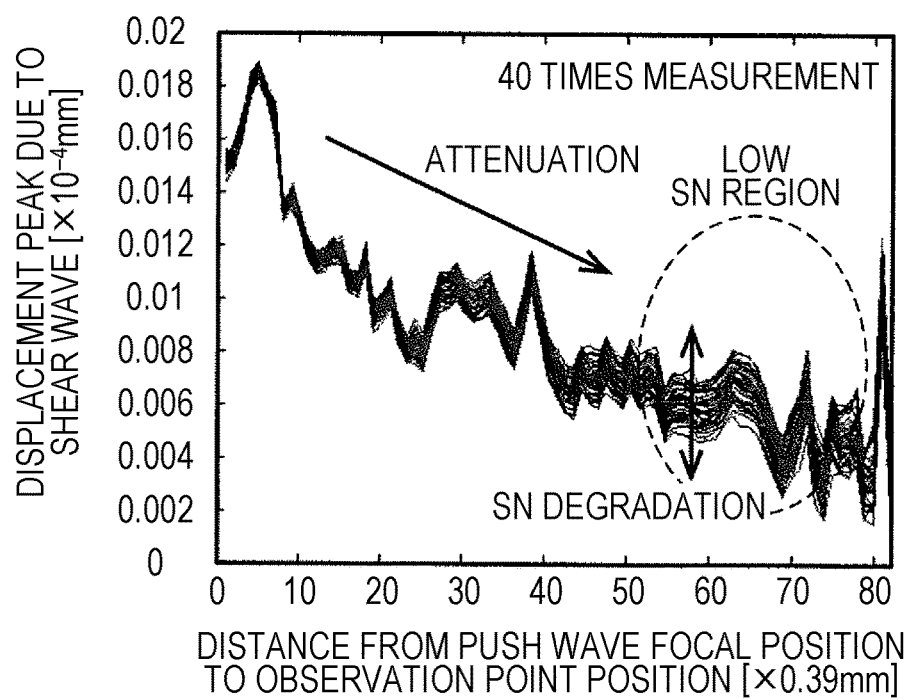
FIG. 10C is a diagram illustrating an experimental result illustrating a relationship between the distance from the push wave focal position FP to the position of the observation point Pij and a variation in the measured elasticity value.

FIG. 10A is a schematic diagram illustrating an example of operation of the propagation analysis of the shear wave, FIG. 10B is a diagram illustrating an experimental result illustrating a relationship between a distance from the push wave focal position FP to the position of the observation point Pij and a measured elasticity value, and FIG. 10C is a diagram illustrating an experimental result illustrating a relationship between the distance from the push wave focal position FP to the position of the observation point Pij and a variation in a displacement peak due to the measured shear wave.

At a position very close to the push wave focal point FP, a displacement of distortion itself of the tissue generated by the push wave is detected, and a propagation phenomenon of the shear wave cannot be captured. That is, physical distortion (initial distortion) induced by the push wave extends not only to the push wave focal point but also to the periphery thereof, and remains for a certain period of time due to the relaxation process after the push wave is stopped. For this reason, as illustrated in FIG. 10B, in a region around the push wave focal point FP, a displacement is detected almost simultaneously at different measurement positions, so that a very high elasticity measurement value may be erroneously detected. In this specification, the region is referred to as an initial distortion region DA. As a result, in the initial distortion region DA, the shear wave propagation cannot be normally detected for a certain period of time. The magnitude of medium distortion near the push wave focal point FP that defines the initial distortion region DA changes depending on an elastic condition of the measurement target, so that it is difficult to predict the magnitude before measurement. For that reason, to avoid influence of the initial distortion due to the push wave, it is desirable to move the measurement position away from the push wave focal point FP.

On the other hand, as illustrated in FIG. 10C, since the shear wave is attenuated with the propagation, when the measurement position of the shear wave is away from the push wave focal point FP, detection accuracy is reduced due to the influence of noise, and a measurement error of elasticity value measurement is expanded. In this specification, the region is referred to as a low SN region.

In addition, when a distance between all the observation points Pij is set as close as possible not to overlap the initial distortion region DA and the low SN region, there is also a problem that an effect of statistical processing is reduced when a representative value is obtained of the elasticity value in the region of interest roi.

For this reason, there has been a problem that accurate measurement cannot be performed regardless of the measurement target in a conventional method in which the measurement region is fixed uniformly for the push wave focal point FP.

Thus, in the present disclosure, the signal to noise ratio for the measurement of the shear wave is sufficiently ensured by providing the evaluator 108 and evaluating the measurement quality, and reliability of the elasticity measurement is improved by appropriately setting the positional relationship between the push wave focal point FP and the measurement region depending on the mechanical property of the measurement target so that the elasticity measurement is not affected by the initial distortion of the push wave.

The evaluator 108 obtains, from the speed calculator 107, the propagation speed in the evaluation target division to be evaluated, and the time-series data of the amount of displacement of the observation point corresponding to the evaluation target division, and calculates the signal level, and/or the noise level. The propagation speed in the evaluation target division is a propagation speed corresponding to a division for evaluating the measurement quality of the propagation speed in the region of interest roi, among the propagation speeds vi(i+1) calculated for divisions between the plurality of (n) observation points Pij and the adjacent observation point P(i+1)j in the region of interest.

Figure 11:
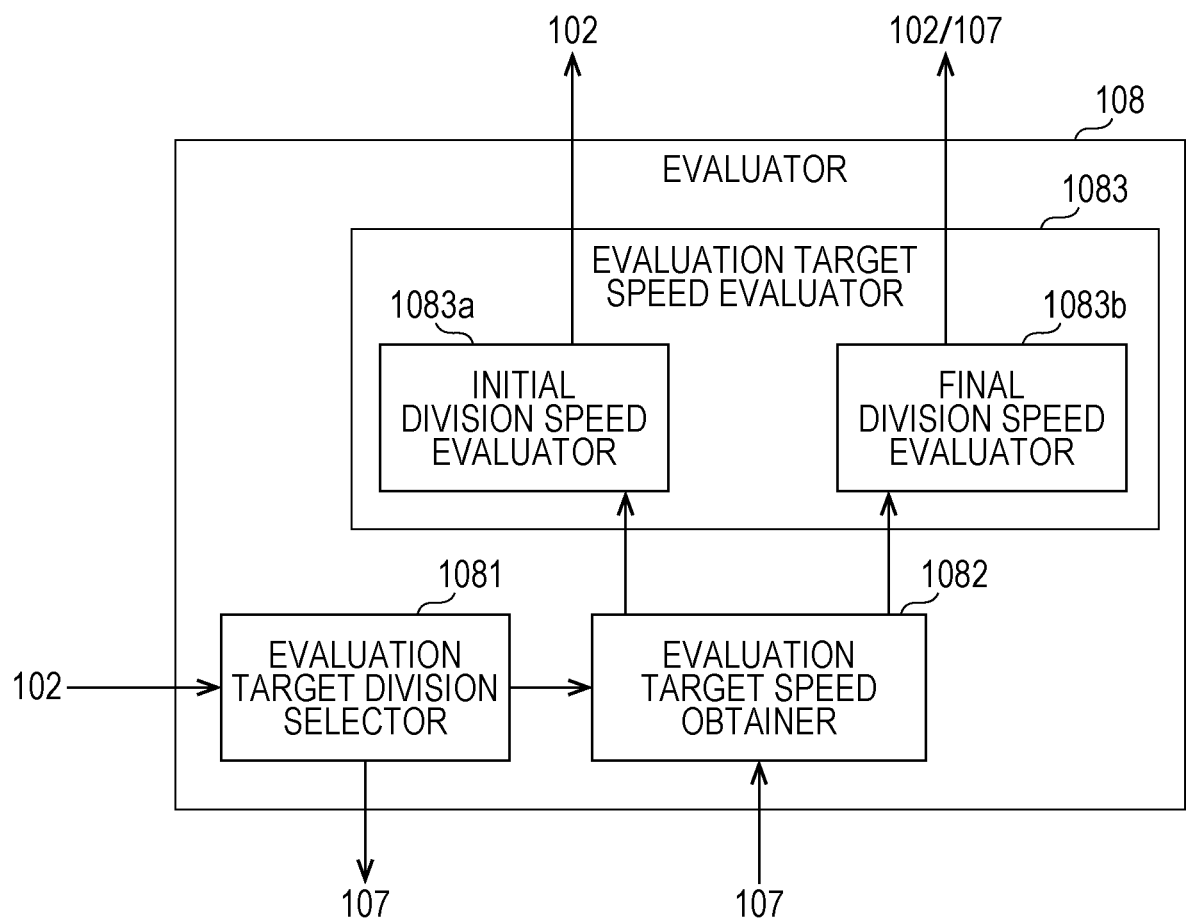
FIG. 11 is a functional block diagram illustrating a configuration of an evaluator.

FIG. 11 is a functional block diagram illustrating a configuration of the evaluator 108. FIGS. 12A to 12C are schematic diagrams each illustrating a positional relationship between the region of interest roi, the push wave focal point FP, and the observation point Pij in operation of the ultrasonic diagnostic apparatus 100.

As illustrated in FIG. 11, the evaluator 108 includes an evaluation target division selector 1081, an evaluation target speed obtainer 1082, and an evaluation target speed evaluator 1083. As a result, it can be detected whether or not the plurality of observation points Pij set in the region of interest is included in either the initial distortion region DA affected by the initial distortion due to the push wave or the low SN region in which the shear wave is attenuated.

The evaluation target division selector 1081 obtains positions of the push wave transmission focal point FP and the observation point Pij from the position determiner 102, and selects an evaluation target division on the basis of a flow of the SWS sequence described later. Specifically, the evaluation target division selector 1081 selects a first division $R_{1,2}$ (i=1) closest to the push wave transmission focal point FP as the evaluation target division to evaluate whether or not the observation point Pij (i=1 to n) is included in the initial distortion region DA. Alternatively, the first division $R_{1,2}$ (i=1) and a second division $R_{2,3}$ (i=2) may be selected. In addition, the evaluation target division selector 1081 selects a final division $R_{n-1,n}$ (i=n−1) farthest from the push wave transmission focal point FP as the evaluation target division to evaluate whether or not the observation point Pij is included in the low SN region.

The evaluation target division selector 1081 outputs a selection result of the selected evaluation target division to the speed calculator 107.

On the basis of an instruction from the evaluation target division selector 1081, the evaluation target speed obtainer 1082 obtains, from the speed calculator 107, the propagation speeds v12 and v23 corresponding to the evaluation target divisions, or the time-series data of the amount of displacement of the observation point corresponding to the evaluation target division, and outputs the data to the evaluation target speed evaluator 1083.

The evaluation target speed evaluator 1083 is a circuit that evaluates the propagation speed and outputs an evaluation result, and includes an initial division speed evaluator 1083a and a final division speed evaluator 1083b.

The initial division speed evaluator 1083a performs evaluation depending on whether or not the propagation speed v12 corresponding to the first division $R_{1,2}$ exceeds a predetermined reference value. In a case where the first division $R_{1,2}$ is included in the initial distortion region DA as illustrated in FIG. 12A, a very high elasticity measurement value is detected in the first division $R_{1,2}$, so that the initial division speed evaluator 1083a detects the case depending on whether or not the propagation speed v12 corresponding to the first division $R_{1,2}$ exceeds the predetermined reference value.

Further, the initial division speed evaluator 1083a may perform rough screening by the absolute value in the first division $R_{1,2}$, and then perform evaluation depending on whether or not a difference obtained by subtracting the propagation speed v23 corresponding to the second division $R_{2,3}$ from the propagation speed v12 corresponding to the first division $R_{1,2}$ exceeds a predetermined reference value. As a result, more accurate evaluation can be performed.

When the evaluation result does not satisfy the requirement (inappropriate), the initial division speed evaluator 1083a outputs the evaluation result to the position determiner 102.

The final division speed evaluator 1083b evaluates whether or not a variation is excessive in the measurement signal value of the time-series data of the amount of displacement of the observation point corresponding to the final division $R_{n-1,n}$. At this time, when there is a plurality of observation points corresponding to the final division $R_{n-1,n}$, an average value in these observation points may be evaluated. In a case where the final division $R_{n-1,n}$ is included in the low SN region in which the shear wave is attenuated as illustrated in FIG. 12B, a low value is detected as a measurement quality value (for example, a parameter based on one or more elements selected from a variance value, a signal level, and a noise level) of the time-series data of the amount of displacement of the observation point corresponding to the final division $R_{n-1,n}$, so that the final division speed evaluator 1083b detects the case depending on whether or not the measurement quality value of the time-series data of the amount of displacement of the observation point corresponding to the final division $R_{n-1,n}$ is greater than or equal to a predetermined reference value.

Alternatively, the final division speed evaluator 1083b may obtain an acoustic ray signal on which the amount of displacement of the observation point corresponding to the final division depends, and evaluate whether a measurement quality value of the acoustic ray signal is greater than or equal to a predetermined reference value. In a case where the final division $R_{n-1,n}$ is included in the low SN region, a low value is detected as the measurement quality value of the acoustic ray signal corresponding to the final division $R_{n-1,n}$. For that reason, the final division speed evaluator 1083b may detect the case depending on whether or not the measurement quality value of the acoustic ray signal corresponding to the final division $R_{n-1,n}$ is greater than or equal to the predetermined reference value.

Note that, in the above description, there is a relationship that the measurement quality value decreases as the variance value increases, as the signal level decreases, and as the noise level increases in the time-series data of the amount of displacement or the measurement signal value of the acoustic ray signal.

The final division speed evaluator 1083b outputs the evaluation result to the position determiner 102 when the evaluation result does not satisfy the requirement (inappropriate), and outputs the evaluation result to the speed calculator 107 when the evaluation result satisfies the requirement (appropriate).

(Change of Position of Transmission Focal Point FP of Push Wave or Observation Point Pij)

In addition, in the second and subsequent measurements, the push wave focal position determiner 102a inputs the evaluation result of the measurement value of the propagation speed from the evaluator 108, and the position information of the region of interest roi from the control unit 111, and changes the position of the transmission focal point FP of the push wave as described below.

Specifically, when the first division $R_{1,2}$ is included in the initial distortion region DA as illustrated in FIG. 12A, the push wave focal position determiner 102a obtains the evaluation result that the evaluation result does not satisfy the requirement (inappropriate) from the initial division speed evaluator 1083a. The push wave focal position determiner 102a changes the push wave focal point FP so that the push wave focal point FP is moved away from the position of the observation point Pij. As a result, as illustrated in FIG. 12C, the position of the observation point Pij can be reset to a position where the influence of the initial distortion due to the push wave is avoided.

Alternatively, when the final division $R_{n-1,n}$ is included in the low SN region as illustrated in FIG. 12B, and the evaluation result that the evaluation result does not satisfy the requirement (inappropriate) is obtained from the final division speed evaluator 1083b, the push wave focal position determiner 102a changes the push wave focal point FP so that the push wave focal point FP is brought close to the observation point Pij. As a result, as illustrated in FIG. 12C, the position of the observation point Pij can be reset to a position not included in the low SN region.

In addition, in the second and subsequent measurements, the observation point position determiner 102b inputs the evaluation result of the measurement value of the propagation speed from the evaluator 108 and the position information of the region of interest roi from the control unit 111, and may change the position of the observation point Pij as described below.

Specifically, when the first division $R_{1,2}$ is included in the initial distortion region DA as illustrated in FIG. 12A, and the evaluation result that the evaluation result does not satisfy the requirement (inappropriate) is obtained from the initial division speed evaluator 1083a, the observation point position determiner 102b may change the position of the observation point Pij that is the measurement position so that the position is moved away from the push wave focal point FP to avoid the influence of the initial distortion due to the push wave. As a result, as illustrated in FIG. 12C, the position of the observation point Pij can be reset to a position where the influence of the initial distortion due to the push wave is avoided.

Alternatively, when the final division $R_{n-1,n}$ is included in the low SN region as illustrated in FIG. 12B, and the evaluation result that the evaluation result does not satisfy the requirement (inappropriate) is obtained from the final division speed evaluator 1083b, the observation point position determiner 102b may change the position of the observation point Pij so that the position is brought close to the push wave focal point FP to avoid influence of the low SN region. As a result, as illustrated in FIG. 12C, the position of the observation point Pij can be reset to a position not included in the low SN region.

(Others)

The ultrasonic diagnostic apparatus 100 may include a B-mode image generation unit (not illustrated) that generates a B-mode tomographic image from the sequence of the acoustic ray signal frame data dsl, and a display control unit (not illustrated) that generates the B-mode tomographic image or the image in which elastic modulus information is superimposed on the B-mode tomographic image and causes the display unit 114 to display the image. The B-mode image generation unit obtains one frame of the acoustic ray signal frame data dsl included in the sequence of the acoustic ray signal frame data dsl. Then, the B-mode image generation unit converts the acoustic ray signal frame data dsl into luminance signal frame data bll by performing envelope detection and logarithmic compression, and outputs the luminance signal frame data bll to the display control unit. The display control unit (not illustrated) obtains the luminance signal frame data bll from the B-mode image generation unit and elastic modulus data elf from the speed calculator 107, performs coordinate transformation, and generates the B-mode image, or the image in which the elastic modulus data is superimposed on the B-mode image.

<Operation of Ultrasonic Diagnostic Apparatus 100>

Operation will be described of an integrated SWS sequence of the ultrasonic diagnostic apparatus 100 having the above configuration.

(Outline of Operation)

Figure 13:
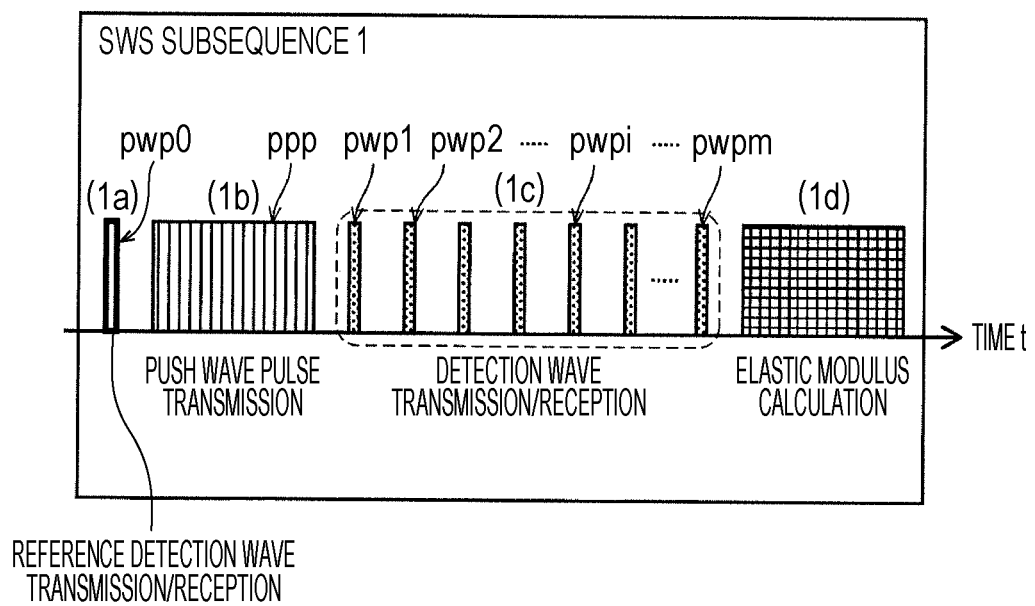
FIG. 13 is a schematic diagram illustrating an outline of steps of an integrated SWS sequence in the ultrasonic diagnostic apparatus.

FIG. 13 is a schematic diagram illustrating an outline of steps of the integrated SWS sequence in the ultrasonic diagnostic apparatus 100. The SWS sequence by the ultrasonic diagnostic apparatus 100 includes: a step of setting the region of interest roi; a step of performing reference detection wave transmission/reception, and obtaining the reference acoustic ray signal frame data ds0 for extracting the displacement due to the shear wave corresponding to each subsequent transmission event; a step of transmitting the push wave pulse ppp to transmit the push wave pp focused on a specific part FP within the subject to excite the shear wave in the subject; a step of performing detection wave pulse pwpl transmission and reception in which transmission and reception of the detection wave pwpl passing through the region of interest roi is repeated multiple times; and a step of elastic modulus calculation for calculating a propagation speed and an elastic modulus of the shear wave by performing a shear wave propagation analysis.

(Operation of SWS Sequence)

Hereinafter, operation will be described of ultrasonic elastic modulus measurement processing after the B-mode image in which the tissue is drawn on the basis of a reflection component from the tissue of the subject on the basis of a known method is displayed on the display unit 114.

Note that, frame data of the acoustic ray signal is generated in a time series on the basis of the reflection component from the tissue of the subject on the basis of transmission and reception of the ultrasonic waves performed in the transmission unit 104 and the detection wave reception unit 105 without the push wave pulse ppp transmitted, and the acoustic ray signal is subjected to processing such as envelope detection and logarithmic compression to be converted into a luminance signal, and then the luminance signal is subjected to coordinate transformation into a rectangular coordinate system to generate frame data of the B-mode image. The B-mode image in which the tissue of the subject is drawn is displayed on the display unit 114.

Figure 14:
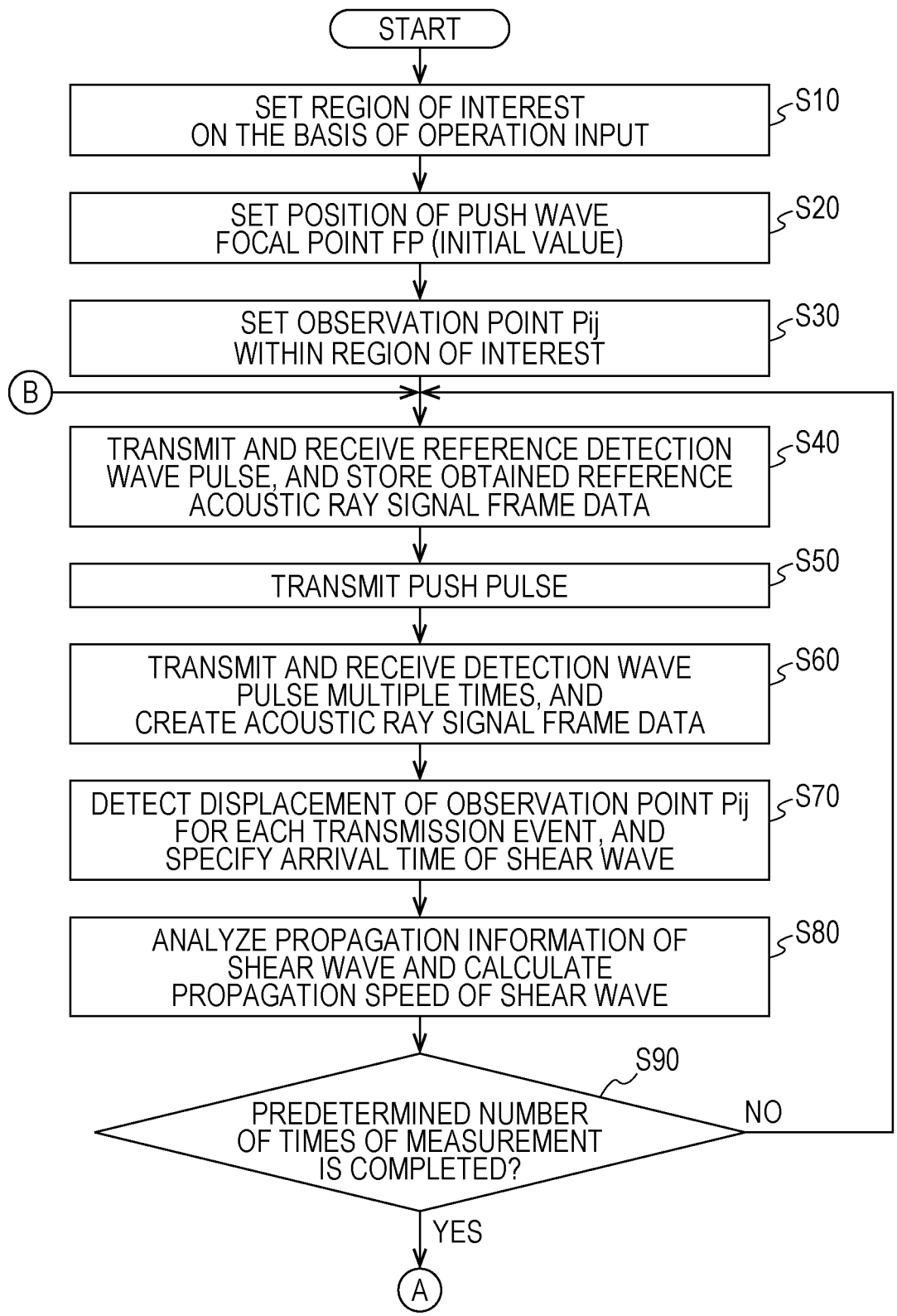
FIG. 14 is a flowchart illustrating operation of SWSM processing in the ultrasonic diagnostic apparatus.
Figure 15:
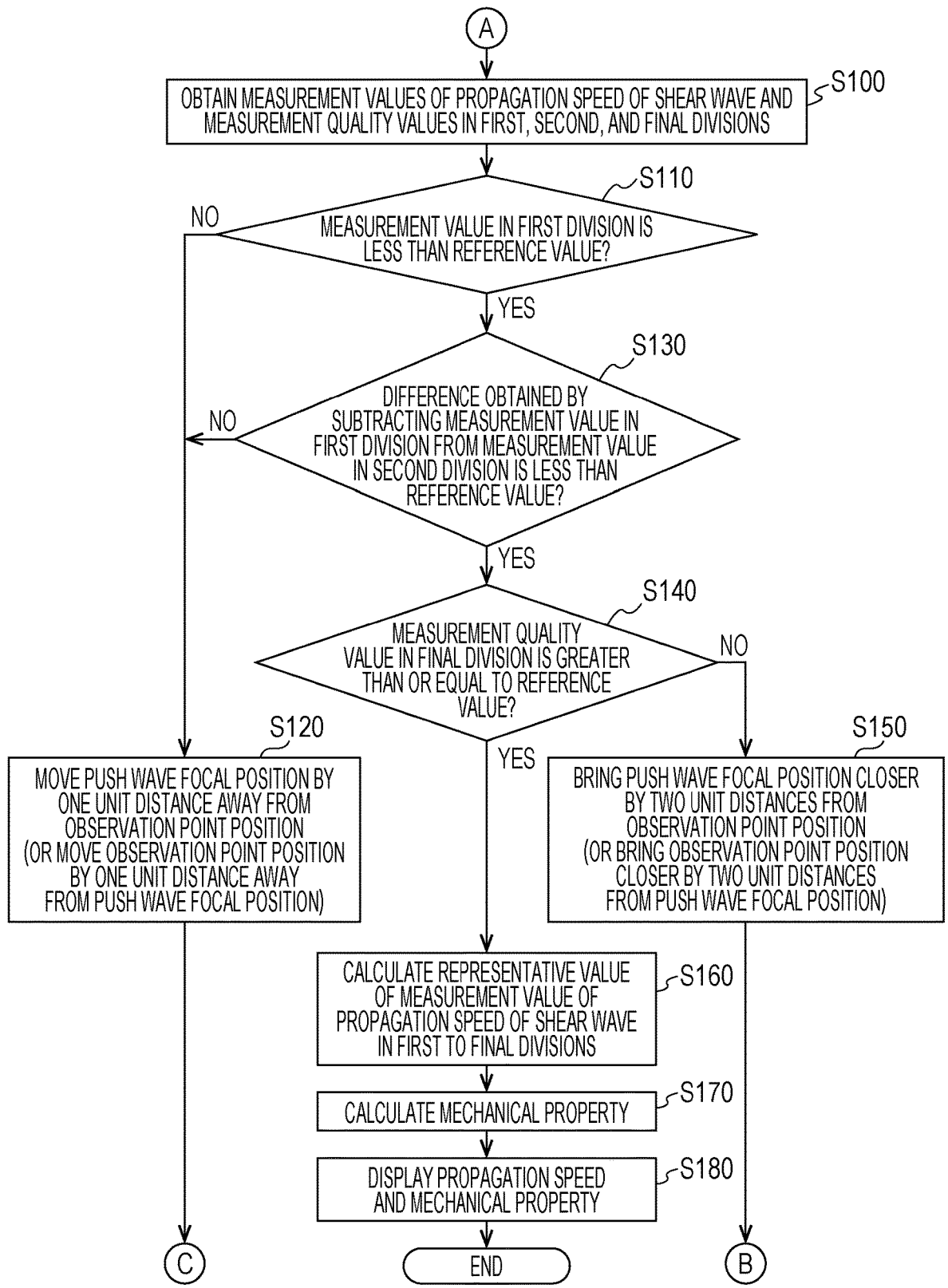
FIG. 15 is a flowchart illustrating the operation of the SWSM processing in the ultrasonic diagnostic apparatus.

FIGS. 14 and 15 are flowcharts illustrating operation of SWSM processing in the ultrasonic diagnostic apparatus 100.

First, in step S10, a region of interest is set on the basis of an operation input from a user. More specifically, in a state in which the B-mode image that is a tomographic image of the subject obtained in real time by the probe 101 is displayed on the display unit 114, the control unit 111 uses information designated by the operator from the operation input unit 113 as an input, and sets the region of interest roi representing an analysis target range within the subject with a position of the probe 101 as a reference.

The designation of the region of interest roi by the operator is performed by, for example, displaying the latest B-mode image recorded in the data storage unit 112 on the display unit 114, and designating the region of interest roi through an input unit (not illustrated) such as a touch panel and a mouse. Here, the region of interest roi is, for example, a fixed range away from the center in the row direction of the B-mode image.

Next, in step S20, the control unit 111 determines the positions fx and fz of the transmission focal point FP of the push pulse. Specifically, the push wave focal position determiner 102a obtains information indicating the region of interest roi from the control unit 111, and determines the positions fx and fz of the transmission focal point FP of the push wave pulse ppp. In this example, as an example, as illustrated in FIG. 3A, the row direction transmission focal position fx coincides with the row direction center position of the push wave transmission transducer row Px, and the depth direction transmission focal position fz is near the region of interest roi. However, the positional relationship between the region of interest roi and the transmission focal point FP is not limited to the above, and may be changed as appropriate depending on the form or the like of the part to be examined of the subject. The information indicating the position of the transmission focal point FP is output to the push wave generation unit 103a, and the push wave generation unit 103a sets transmission conditions such as the push wave transmission transducer row Px, the pulse width PW of the push wave pulse ppp, and the application start time PT. In this example, as an example, as illustrated in FIG. 3A, the push wave transmission transducer row Px is all of the plurality of transducers 101a, but may be a part thereof. The push wave generation unit 103a outputs these pieces of information to the transmission unit 104 as the transmission control signal.

Next, in step S30, the observation point position determiner 102b sets the observation points Pij within the region of interest roi. In this example, as illustrated in FIG. 9A, the observation points Pij are arranged at equal intervals on the straight line Lx extending in the X direction within the region of interest roi. Note that, the observation points Pij are preferably present on a straight line extending in the Z direction passing through the center of any of the reception transducers Rpk.

Next, in step S40, the reference detection wave pulse is transmitted and received, and the obtained reference acoustic ray signal frame data is stored. Specifically, the detection wave pulse is caused to be transmitted into the region of interest roi, and acoustic ray signal frame data is generated for the observation points Pij set in step S30 and stored in the data storage unit 112 as reference acoustic ray signal frame data.

Next, in step S50, the push pulse is transmitted. Specifically, the transmission unit 104 generates a transmission profile on the basis of the transmission control signal including the information indicating the position of the transmission focal point FP and the push wave transmission transducer row Px, the pulse width PW of the push wave pulse ppp, and the application start time PT obtained from the push wave generation unit 103a. The transmission profile includes the pulse signal sp and the delay time tpk for each transmission transducer included in the push wave transmission transducer row Px. Then, the push wave pulse ppp is supplied to each transmission transducer on the basis of the transmission profile. Each transmission transducer transmits the push wave pp of a pulse form focused on the specific part within the subject.

Figure 16A:
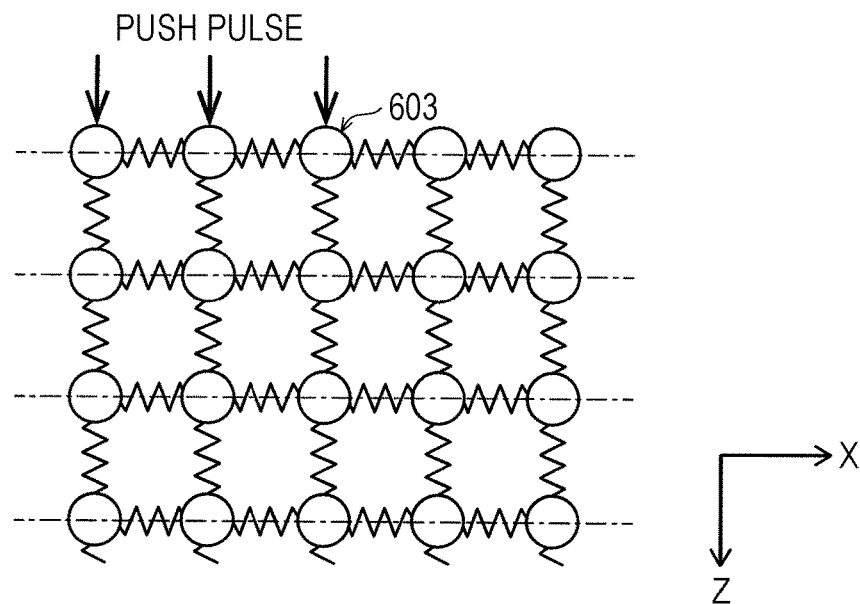
FIGS. 16A to 16C are schematic diagrams illustrating a state of generation of the shear wave by a push wave pulse pp.
Figure 16B:
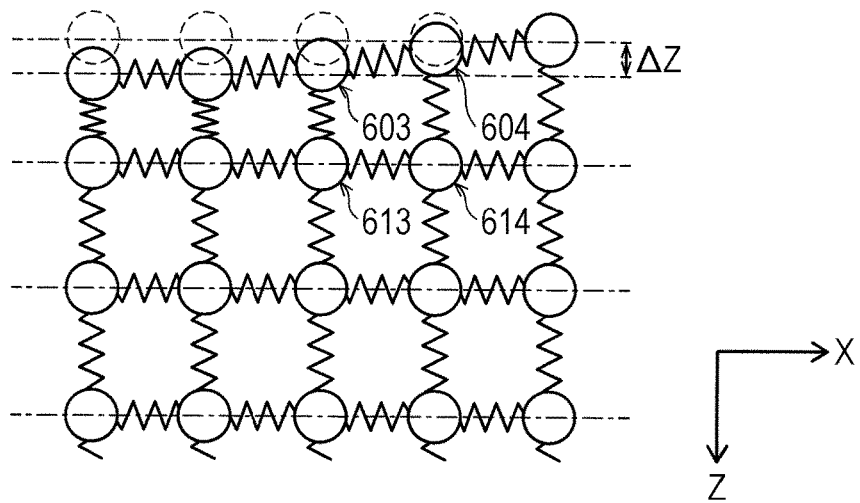
Figure 16C:
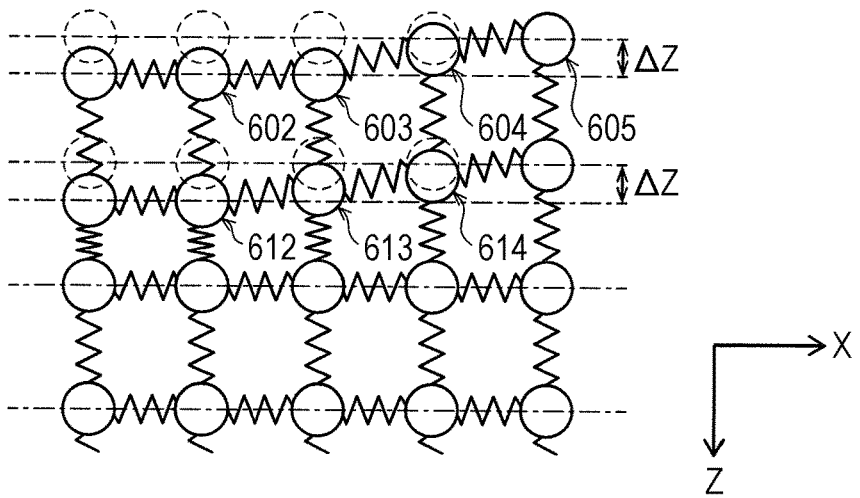

Here, generation of the shear wave by the push wave pp will be described with reference to schematic diagrams of FIGS. 16A to 16C. FIGS. 16A to 16C are spring models illustrating a mechanism of shear wave excitation by the push wave pp. In FIGS. 16A to 16C, the tissue within the subject having elasticity is illustrated as a plurality of balls connected by springs, and each of the balls correspond to each position of the tissue within the subject.

First, the push wave pp is applied to a focus part in the subject corresponding to the transmission focal point FP while the probe 101 is in close contact with a skin surface. As a result, a ball 603 corresponding to the focus part moves in the Z direction due to the push pulse. Then, as illustrated in FIG. 16B, a ball 604 connected to the ball 603 is pulled in the Z direction, and balls 613 and 614 are pushed in the Z direction by the balls 603 and 604, respectively. As a result, as illustrated in FIG. 16C, balls 612 and 613 pushed by balls 602 and 603 pushed directly by the push pulse move in the Z direction and push the other balls, and the ball 614 pushed by the ball 604 in the Z direction and pulled by the ball 613 in the Z direction moves in the Z direction. With this operation, vibration in the Z direction propagates to the positions of the balls 604 and 614 that are not directly pressed by the push pulse. That is, the focus part is pressed in the Z direction, whereby the focus part vibrates in the Z direction, the tissue adjacent in the X direction is pulled in the Z direction, and the tissue also vibrates in the Z direction. Further, chain motion occurs in which the tissue adjacent in the X direction to the tissue vibrating in the Z direction is pulled in the Z direction and vibrates in the Z direction. Further, such operation occurs repeatedly, whereby the vibration in the Z direction propagates in the X direction, that is, a phenomenon occurs in which the shear wave propagates in the X direction.

Returning to FIG. 14, description will be continued.

Next, in step S60, the detection wave pulse pwpl is transmitted and received multiple times to the region of interest roi, and the obtained sequence of the acoustic ray signal frame data dsl is stored. Specifically, the transmission unit 104 causes the transducer included in the detection wave transmission transducer row Tx to transmit the detection wave pulse pwpl toward the subject, and the detection wave reception unit 105 generates the acoustic ray signal frame data dsl on the basis of the reflected wave ec received by the transducer included in the detection wave pulse reception transducer row Rx. From immediately after the transmission of the push wave pp is completed, the above processing is repeated, for example, 10,000 times per second. As a result, the acoustic ray signal frame data dsl within the region of interest roi is repeatedly generated from immediately after the generation of the shear wave until the propagation ends. The generated sequence of the acoustic ray signal frame data dsl is output to the data storage unit 112 and stored.

More specifically, the following processing is performed. First, the detection wave reception unit 105 calculates, for an arbitrary observation point Pij existing within the region of interest roi, a transmission time in which the transmitted ultrasonic wave reaches the observation point Pij in the subject. Next, the detection wave reception unit 105 sets the detection wave pulse reception transducer row Rx, and calculates a reception time in which the reflected detection wave from the observation point Pij reaches each of reception wave transducers Rwk included in the detection wave pulse reception transducer row Rx. Then, the detection wave reception unit 105 calculates the amount of delay for each observation point Pij and for each reception transducer Rwk from the transmission time and the reception time, and identifies the received signal from the observation point Pij, for each observation point Pij, from the acoustic ray signal frame data dsl. Next, the detection wave reception unit 105 weights and adds the received signals identified for each observation point Pij to calculate the acoustic ray signal for the observation point Pij. Here, for the weighting, for example, the reception apodization is made such that the weighting of the transducer positioned at the center in the X direction of the detection wave pulse reception transducer row Rx is maximized. The detection wave reception unit 105 stores the calculated acoustic ray signal in the data storage unit 112.

Next, in step S70, the amount of displacement of each observation point Pij within the region of interest roi is detected for each transmission event, and the arrival time of the shear wave is specified. Specifically, in the first transmission event, the speed calculator 107 performs correlation processing between the acoustic ray signal frame data dsl and the reference acoustic ray signal frame data ds0 for each observation point Pij, and detects an amount of positional displacement for each observation point Pij. Further, this processing is performed for all transmission events, whereby the amount of displacement for each transmission event is detected for each observation point Pij. Then, for each observation point Pij, a transmission event is specified in which the size of the amount of displacement is maximized, and the time at which the transmission event is performed is specified as the peak time.

Next, in step S80, the propagation analysis of the shear wave is performed. Specifically, the speed calculator 107 uses the peak time for each observation point Pij specified in step S70 as an index, and divides a distance between two observation points Pij adjacent in the row direction by a time difference between the peak times, thereby estimating the propagation speed of the shear wave. In the embodiment, as illustrated in FIG. 9D, the observation points $P_{11}$, $P_{12}$, and $P_{13}$ arranged in the row direction are plotted on a graph having the vertical axis of the shear wave propagation path axis d, and the horizontal axis of the peak time. Then, the propagation speed of the shear wave is estimated by calculating an inclination between the observation points (=distance between the observation points/time difference between the peak times). Then, a representative value of the propagation speed of the shear wave is calculated and output as the propagation speed of the shear wave in the region of interest roi. As the representative value, for example, a median value or an average value may be used. Note that, the mechanical property calculator 109 may calculate a mechanical property value of the subject in the region of interest roi on the basis of the propagation speed of the shear wave in the region of interest roi.

Next, the control unit 111 determines whether or not a predetermined number of times of measurement required to evaluate the variation (measurement quality) in the propagation speed of the shear wave is completed (step S90). The predetermined number of times may be 3 times or more and 100 times or less. If not completed, the process returns to step S40 to calculate the propagation speed of the shear wave (steps S40 to S80), and if completed, the process proceeds to step S100 in FIG. 15. Note that, FIG. 15 is the flowchart illustrating the operation of the SWSM processing following FIG. 14.

In step S100, the evaluation target division selector 1081 selects the first division, the second division, and the final division as the evaluation target divisions; the evaluation target speed obtainer 1082 obtains measurement values of the propagation speed of the shear wave and measurement quality values in the first division, the second division, and the final division from the speed calculator 107; and the initial division speed evaluator 1083a determines whether or not the measurement value in the first division is less than a reference value (step S110).

In a case where the measurement value is not less than the reference value, the initial division speed evaluator 1083a determines that the first division $R_{1,2}$ is included in the initial distortion region DA as illustrated in FIG. 12A. In this case, the push wave focal position determiner 102a determines a position of a new push wave focal point FP obtained by moving the position of the push wave focal point FP by one unit distance from the position of the observation point Pij (step S120), and in a case where the measurement value is less than the reference value, the process proceeds to step S130.

Note that, in step S120, instead of or in addition to the above processing, the observation point position determiner 102b may perform processing of determining a position of a new observation point Pij obtained by moving the position of the observation point Pij by one unit distance from the position of the push wave focal point FP. Here, the unit distance is the minimum distance when the position of the push wave focal point FP or the observation point Pij is changed, and may be set to ¼ to ½ of the distance between adjacent observation points Pij.

In step S130, the initial division speed evaluator 1083a determines whether or not a difference obtained by subtracting the measurement value in the first division from the measurement value in the second division is less than a reference value, and in a case where the difference is not less than the reference value, the initial division speed evaluator 1083a determines that the first division $R_{1,2}$ is included in the initial distortion region DA as illustrated in FIG. 12A, and performs the processing of step S120 described above. In a case where the difference is less than the reference value, the initial division speed evaluator 1083a determines that the first division $R_{1,2}$ is not included in the initial distortion region DA, and proceeds to step S140.

In step S140, the final division speed evaluator 1083b determines whether or not the measurement quality value in the final division is greater than or equal to a reference value. In a case where the difference is less than the reference value, it is determined that the final division $R_{n-1,n}$ is included in the low SN region in which the shear wave is attenuated as illustrated in FIG. 12B, and the push wave focal position determiner 102a determines a position of a new push wave focal point FP obtained by bringing the position of the push wave focal point FP closer by two unit distances from the position of the observation point Pij (step S150). In a case where the difference is greater than or equal to the reference value, the final division speed evaluator 1083b determines that the final division $R_{n-1,n}$ is not included in the low SN region, and proceeds to step S160.

Note that, also in step S150, instead of or in addition to the above processing, the observation point position determiner 102b may perform processing of determining a new observation point Pij obtained by bringing the position of the observation point Pij closer by two unit distances from the position of the push wave focal point FP.

In step S160, the propagation speed calculator 1072 calculates and outputs a representative value of the propagation speed v of the shear wave as the shear wave propagation speed vo in the region of interest. The representative value includes, for example, an average value and a median value.

Next, the mechanical property calculator 109 converts the propagation speed of the shear wave in the region of interest into, for example, a mechanical property value of the subject tissue such as the elastic modulus (step S170), and the propagation speed of the shear wave in the region of interest or the mechanical property value of the tissue is displayed on the display 114 (step S180).

At this time, propagation information of the shear wave may be superimposed and displayed on the B-mode image. Specifically, for example, information indicating the position of the region of interest roi and a value of the elastic modulus are superimposed on the B-mode image. Note that, only the information indicating the position of the region of interest roi may be superimposed on the B-mode image, and the value of the elastic modulus may be displayed around the B-mode image.

With the above, the processing of the SWS sequence illustrated in FIGS. 14 and 15 is completed. Through the above ultrasonic elastic modulus measurement processing, the elastic modulus data elf based on the SWS sequence can be calculated.

SUMMARY

As described above, the ultrasonic diagnostic apparatus 100 according to the present embodiment includes: the position determiner 102; the shear wave displacement obtainer 110; the speed calculator 107; and the evaluator 108 that evaluates the value of the propagation speed calculated by the ultrasonic elastic modulus measurement to create the evaluation result, and when the evaluation result does not satisfy a predetermined requirement, the position determiner 102 determines a new focal position and positions of a new plurality of observation points in which at least one of the focal position or the plurality of observation points is changed on the basis of the evaluation result, and for the new focal position and the positions of the new plurality of observation points determined, the shear wave displacement obtainer 110 calculates the amount of displacement, and the speed calculator 107 calculates the propagation speed, and when the evaluation result satisfies the requirement, the speed calculator 107 calculates the propagation speed value of the region of interest on the basis of the propagation speeds with respect to the plurality of observation points.

With such a configuration, in the ultrasonic elastic modulus measurement that obtains the absolute value of the mechanical property of the tissue from the narrow region of interest, the reliability of the absolute value of the measurement signal value of the mechanical property can be improved by improving the accuracy of detecting the amount of displacement.

That is, the propagation analysis of the shear wave is performed by setting the position of the observation point Pij to positions not included in the initial distortion region DA or the low SN region, whereby the required signal to noise ratio can be maintained in the measurement value while avoiding the influence of the initial distortion due to the push wave, and the accuracy can be improved of the propagation analysis of the shear wave. In addition, since the number of observation points Pij in the narrow region of interest is limited to the number corresponding to the calculation capability of the speed calculator 107, processing can be performed on the basis of the observation points Pij of the number corresponding to the calculation capability of the speed calculator 107, and the shortage of the calculation capacity can be suppressed.

<<Modifications>>

Although the ultrasonic diagnostic apparatus according to the embodiment has been described, the present disclosure is not limited to the above-described first embodiment at all except for its essential characteristic components. For example, an embodiment obtained by applying various modifications to the first embodiment by those skilled in the art, or an embodiment implemented by arbitrarily combining the components and functions of the first embodiment without departing from the spirit of the present invention are also included in the present disclosure. Hereinafter, modifications will be described of the ultrasonic diagnostic apparatus, as an example of such an embodiment.

<First Modification>

Figure 17A:
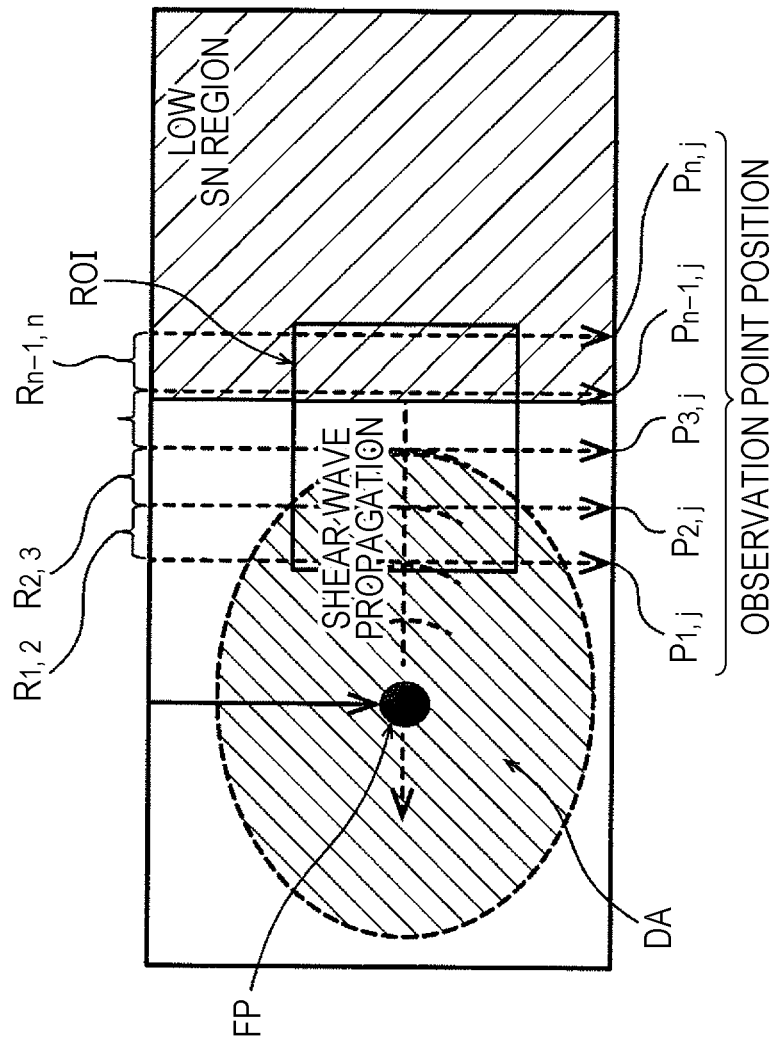
FIGS. 17A to 17C are schematic diagrams each illustrating a positional relationship between the region of interest roi, the push wave focal point FP, and the observation points Pij in operation of an ultrasonic diagnostic apparatus according to a first modification.
Figure 17B:
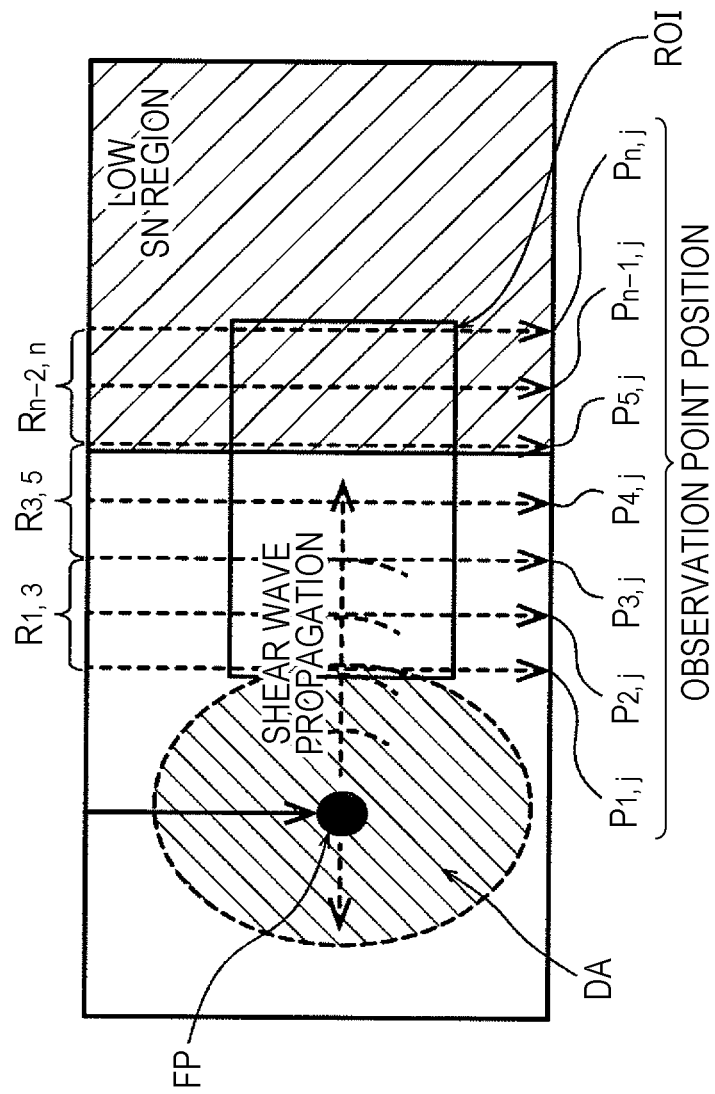
Figure 17C:
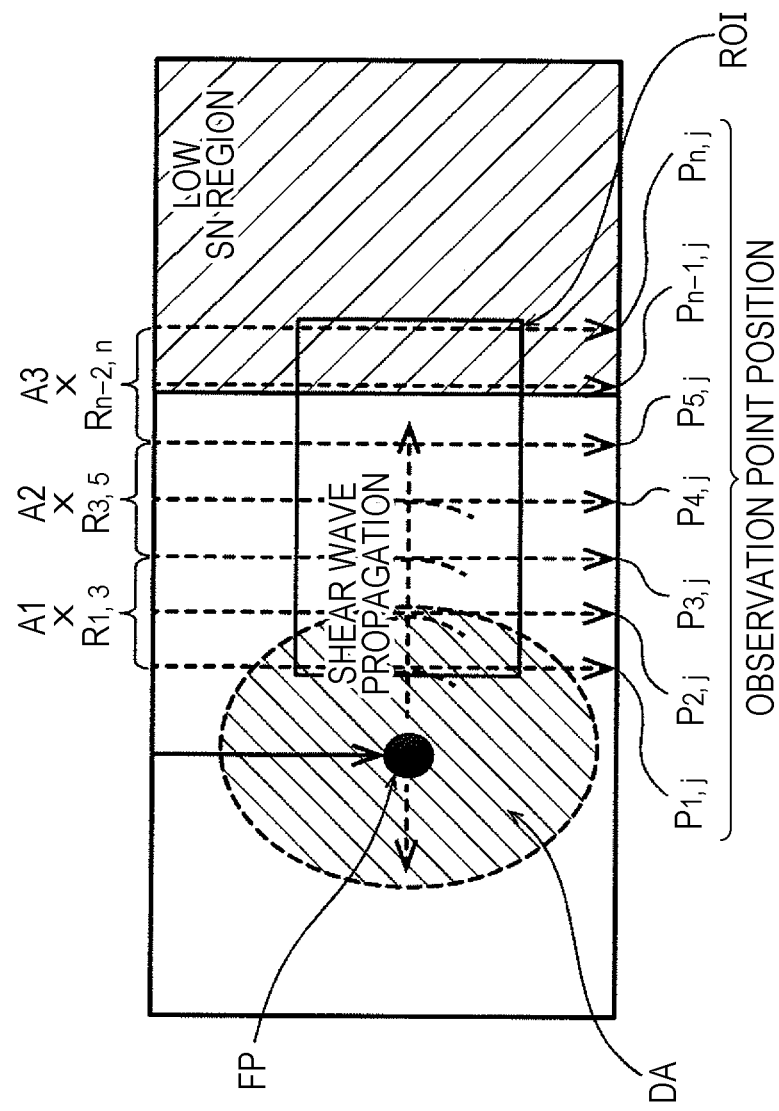
Figure 18:
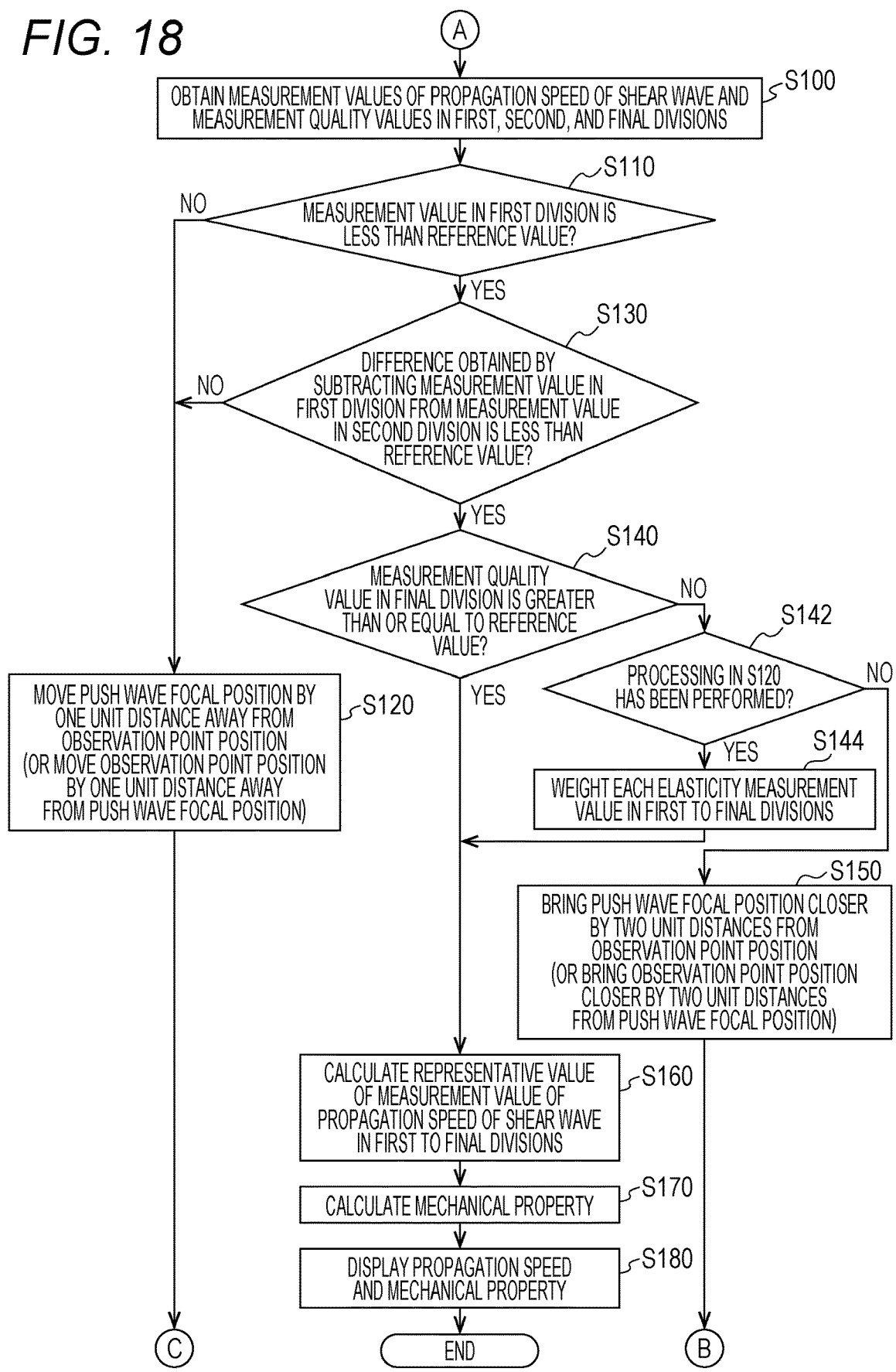
FIG. 18 is a flowchart of a part corresponding to FIG. 15 in the embodiment in the operation of the SWSM processing in the ultrasonic diagnostic apparatus according to the first modification.

FIGS. 17A to 17C are schematic diagrams each illustrating a positional relationship between the region of interest roi, the push wave focal point FP, and the observation point Pij in operation of an ultrasonic diagnostic apparatus according to a first modification. FIG. 18 is a flowchart of a part different from the embodiment, in the operation of the SWSM processing in the ultrasonic diagnostic apparatus according to the first modification.

In the ultrasonic diagnostic apparatus according to the first modification, a configuration is adopted in which, in a case where a distance between the initial distortion region DA and the low SN region is short, and the first division $R_{1,2}$ is included in the initial distortion region DA, and the final division $R_{n-1,n}$ is included in the low SN region as illustrated in FIG. 17A, the propagation speed calculator 1072 calculates, as the propagation speed of the shear wave in the region of interest, a representative value of the propagation speed v by multiplying the propagation speed calculated for each of the divisions between the plurality of (n) observation points Pij in the region of interest by a weight sequence in which the weight is increased of the central part of the region of interest along the propagation direction of the shear wave, as illustrated in FIG. 17C. The representative value includes, for example, an average value and a median value. At this time, in the ultrasonic diagnostic apparatus according to the first modification, a configuration may be adopted in which the distance between the observation points Pij is made closer and the number of observation points Pij is increased, and a representative value is obtained of the elasticity value in the region of interest roi as illustrated in FIGS. 17B and 17C. In addition, a configuration may be adopted in which a plurality of divisions between adjacent observation points Pij is put together, and a united division is multiplied by the same weighting factor. In the examples of FIGS. 17B and 17C, two divisions between adjacent observation points Pij are put together, and united divisions are multiplied by the same weighting factors A1, A2, and A3, respectively.

FIG. 18 is the flowchart of a part corresponding to FIG. 15 in the embodiment in the operation of the SWSM processing in the ultrasonic diagnostic apparatus according to the first modification. In the processing in the ultrasonic diagnostic apparatus according to the first modification, a part corresponding to FIG. 14 in the embodiment has the same configuration as FIG. 14. The flowchart of FIG. 18 differs from the flowchart of FIG. 15 in that steps S142 and S144 are provided after step S140. Thus, the different steps will be described below.

In step S140 of FIG. 18, in a case where the measurement quality value in the final division is less than the reference value, the final division speed evaluator 1083b determines that the final division $R_{n-1,n}$ is included in the low SN region as illustrated in FIG. 17B, similarly to the embodiment.

Next, in the ultrasonic diagnostic apparatus according to the first modification, in the determination in step S142, it is determined whether or not the processing in step S120 has already been performed. In a case where the processing has not been performed, the process proceeds to step S150, and the push wave focal position determiner 102a determines a position of a new push wave focal point FP obtained by bringing the position of the push wave focal point FP closer by two unit distances from the position of the observation point Pij.

In the determination in step S142, in a case where the processing in step S120 has already been performed, the evaluator 108 evaluates that it corresponds to the case where the distance between the initial distortion region DA and the low SN region is short, and the first division $R_{1,2}$ is included in the initial distortion region DA, and the final division $R_{n-1,n}$ is included in the low SN region, and the process proceeds to step S144.

In step S144, the propagation speed calculator 1072 multiplies the propagation speeds calculated for the respective divisions, the first division $R_{1,2}$, the second division $R_{2,3}, \ldots R_{n-1,n}$, between the plurality of (n) observation points Pij in the region of interest by the weight sequence in which the weight is increased of the central part of the region of interest along the propagation direction of the shear wave, as illustrated in FIG. 17C.

Next, in step S160, the propagation speed calculator 1072 calculates and outputs a representative value vo of the propagation speed v of the shear wave in the region of interest from the sequence of the propagation speeds multiplied by the weight sequence in step S144.

With such a configuration, also in a case where the distance between the initial distortion region DA and the low SN region is short, and the first division based on the plurality of observation points Pij set in the region of interest is included in the initial distortion region DA, and the final division is included in the low SN region, the weight is increased of the measurement result at the central part of the region of interest along the propagation direction of the shear wave, whereby in the ultrasonic elastic modulus measurement that obtains the absolute value of the mechanical property of the tissue in the narrow region of interest, the reliability of the absolute value of the measurement signal value of the mechanical property can be improved by improving the accuracy of detecting the amount of displacement by making the measurement result of the central part of the region of interest dominant further.

<Other Modifications According to Embodiment>

(1) In the embodiment, the number of the focal points of the push pulse is set to one; however, for example, a plurality of focal points having the same x-coordinate but different z-coordinates may be provided, and control may be performed so that push pulses are sequentially transmitted in ascending order of the z-coordinate or descending order of the z-coordinate, and the shear wave is a virtual plane wave.

(2) In each embodiment, the step of reference detection wave pulse transmission/reception is performed prior to the step of push wave pulse transmission for displacement detection, and the displacement detection unit detects the amount of displacement Ptij of the observation point Pij on the basis of the difference between the acoustic ray signal frame data dsl and the reference acoustic ray signal frame data ds0 formed in the reference detection wave pulse transmission/reception. However, the method for detecting the amount of displacement of the tissue is not limited to this case. For example, the ultrasonic diagnostic apparatus does not perform the step of reference detection wave pulse transmission/reception, and does not generate the reference acoustic ray signal frame data ds0. Then, the displacement detection unit detects the amount of change ΔPtij between transmission events of the amount of displacement Ptij of the observation point Pij on the basis of a difference between the acoustic ray signal frame data dsl and acoustic ray signal frame data ds (l−1) obtained in the immediately preceding transmission event. Then, the amount of displacement Ptij of the observation point Pij may be generated by integrating the amount of change ΔPtij between the plurality of transmission events in the amount of displacement Ptij, for each observation point Pij. Note that, the detection of the amount of change ΔPtij between the transmission events is not limited to that between two consecutive transmission events, and the amount of change ΔPtij of the amount of displacement Ptij of the observation point Pij may be calculated from a difference between arbitrary two acoustic ray signal frame data dsl.

(3) In the ultrasonic diagnostic apparatus according to each embodiment, all or a part of the components may be implemented by one chip or a plurality of chips of integrated circuits, may be implemented by a program of a computer, or may be implemented in any other form. For example, a push wave generation unit and a detection wave generation unit may be implemented by one chip, or a reception beam former unit may be implemented by one chip, and a speed detection unit and the like may be implemented by another chip.

In a case where the components are implemented by the integrated circuit, the components are typically implemented as a Large Scale Integration (LSI). Here, the LSI is also referred to as an IC, system LSI, super LSI, or ultra LSI, depending on the degree of integration.

In addition, a method of circuit integration is not limited to the LSI, and may be implemented by a dedicated circuit or a general-purpose processor. It is also possible to use a Field Programmable Gate Array (FPGA) that can be programmed after manufacturing of the LSI, or a reconfigurable processor capable of reconfiguring connections and settings of circuit cells inside the LSI.

Further, if a circuit integration technology appears that replaces the LSI due to progress of the semiconductor technology or another derivative technology, naturally, integration of functional blocks may be performed by using the integrated circuit technology.

In addition, the ultrasonic diagnostic apparatus according to each embodiment and each modification may be implemented by a program written in a storage medium and a computer that reads and executes the program. The storage medium may be any recording medium such as a memory card or a CD-ROM. In addition, the ultrasonic diagnostic apparatus according to the present invention may be implemented by a program downloaded via a network and a computer that downloads and executes the program from the network.

SUMMARY

The ultrasonic diagnostic apparatus according to the present disclosure is an ultrasonic diagnostic apparatus that calculates a propagation speed of a shear wave by exciting the shear wave within a subject by using an ultrasonic probe, the ultrasonic diagnostic apparatus including: a position determiner that determines a focal position of a push wave for generating a displacement within the subject, and positions of a plurality of observation points in a region of interest indicating an analysis target range within the subject; a shear wave displacement obtainer that causes the ultrasonic probe to perform transmission of a push wave focusing on the focal position, and subsequent to the transmission, causes the ultrasonic probe to transmit a detection wave passing through the region of interest within the subject, and calculates amounts of displacement of tissue of the subject at the plurality of observation points on the basis of a reflected wave obtained by the ultrasonic probe in response to the transmission of the detection wave; a speed calculator that calculates propagation speeds of the shear wave in the tissue of the subject with respect to the plurality of observation points on the basis of the amounts of displacement; and an evaluator that evaluates values of the propagation speeds calculated to create an evaluation result, in which when the evaluation result does not satisfy a predetermined requirement, the position determiner determines a new focal position and positions of a new plurality of observation points in which at least one of the focal position or the positions of the plurality of observation points is changed on the basis of the evaluation result, and for the new focal position and the positions of the new plurality of observation points determined, the shear wave displacement obtainer calculates the amounts of displacement, the speed calculator calculates the propagation speeds, and the evaluator evaluates values of the propagation speeds newly calculated to create an evaluation result, and when the evaluation result satisfies the requirement, the speed calculator calculates a propagation speed value in the region of interest on the basis of the propagation speeds with respect to the plurality of observation points.

With such a configuration, in the ultrasonic elastic modulus measurement that obtains the absolute value of the mechanical property of the tissue from the narrow region of interest, the reliability of the absolute value of the measurement signal value of the mechanical property can be improved by improving the accuracy of detecting the amount of displacement.

In addition, in another aspect, a configuration may be adopted in which: the evaluator includes: an evaluation target division selector that selects an evaluation target division to be evaluated among divisions between adjacent observation points based on the plurality of observation points of which position is determined by the position determiner; an evaluation target speed obtainer that obtains a propagation speed corresponding to the evaluation target division from the propagation speeds with respect to the respective plurality of observation points and sets the propagation speed as an evaluation target speed; and a target speed evaluator that evaluates whether the evaluation target speed is appropriate and satisfies the requirement, or is inappropriate and does not satisfy the requirement.

With such a configuration, it can be detected whether or not the plurality of observation points Pij set in the region of interest is included in either the initial distortion region DA affected by the initial distortion due to the push wave or the low SN region in which the shear wave is attenuated.

In addition, in another aspect, a configuration may be adopted in which: the evaluation target division selector selects a first division closest to the focal position of the push wave; the evaluation target speed obtainer obtains a propagation speed corresponding to the first division and sets the propagation speed as the evaluation target speed; the target speed evaluator outputs an evaluation result as being appropriate when the evaluation target speed is less than a first threshold, and outputs an evaluation result as being inappropriate when the evaluation target speed is greater than or equal to the first threshold; and when the evaluation result is output as being inappropriate, the position determiner determines a new focal position and positions of a new plurality of observation points that are obtained by increasing distances between the focal position and the positions of the plurality of observation points.

With such a configuration, it can be detected whether or not a very high elasticity measurement value is detected in the first division $R_{1,2}$ under the influence of the initial distortion due to the push wave.

In addition, in another aspect, a configuration may be adopted in which: the evaluation target division selector selects a first division closest to the focal position of the push wave, and a second division adjacent to the first division; the evaluation target speed obtainer obtains propagation speeds corresponding to the first division and the second division and sets each of the propagation speeds as the evaluation target speed; the target speed evaluator outputs an evaluation result as being appropriate when the propagation speed corresponding to the second division is greater than or equal to the propagation speed corresponding to the first division, and outputs an evaluation result as being inappropriate when the propagation speed corresponding to the second division is less than the propagation speed corresponding to the first division; and when the evaluation result is output as being inappropriate, the position determiner determines a new focal position and positions of a new plurality of observation points that are obtained by increasing distances between the focal position and the positions of the plurality of observation points.

With this configuration, more accurate evaluation can be performed whether or not a very high elasticity measurement value is detected in the first division $R_{1,2}$ under the influence of the initial distortion due to the push wave.

In addition, in another aspect, a configuration may be adopted in which: the evaluation target division selector selects a final division farthest from the focal position of the push wave; the evaluation target speed obtainer obtains a measurement quality value of time-series data of the amount of displacement at an observation point corresponding to the final division; the target speed evaluator outputs an evaluation result as being appropriate when the measurement quality value is greater than or equal to a second threshold, and outputs an evaluation result as being inappropriate when the measurement quality value is less than the second threshold; and when the evaluation result is output as being inappropriate, the position determiner determines a new focal position and positions of a new plurality of observation points that are obtained by decreasing distances between the focal position and the positions of the plurality of observation points.

In addition, in another aspect, a configuration may be adopted in which the measurement quality value is a parameter based on one or more elements selected from a variance, a signal level, and a noise level of the amounts of displacement or acoustic ray signals on which the amounts of displacement depend.

With such a configuration, it can be detected whether or not the final division $R_{n-1,n}$ is included in the low SN region in which the shear wave is attenuated.

In addition, in another aspect, a configuration may be adopted in which in a case where the target speed evaluator outputs an evaluation result as being inappropriate, and in a case where the plurality of observation points on which the evaluation target division depends is obtained by determination of the new focal position and the positions of the new plurality of observation points by the position determiner having already performed a first change for distances between the focal position and the positions of the plurality of observation points, and in a case where, on the basis of the evaluation result as being inappropriate, the position determiner is prompted to determine a further new focal position and positions of a further new plurality of observation points by performing a second change opposite to the first change for the distances between focal position and the positions of the plurality of observation points, the target speed evaluator outputs an evaluation result as being appropriate regarding the evaluation target division, and the speed calculator calculates a propagation speed value of the region of interest by multiplying the propagation speeds with respect to the plurality of observation points by a weight sequence in which a weight of a central part of the region of interest along a propagation direction is increased.

With such a configuration, also in a case where the distance between the initial distortion region DA and the low SN region is short, and the first division based on the plurality of observation points Pij set in the region of interest is included in the initial distortion region DA, and the final division is included in the low SN region, in the ultrasonic elastic modulus measurement that obtains the absolute value of the mechanical property of the tissue in the narrow region of interest, the reliability of the absolute value of the measurement signal value of the mechanical property can be improved by improving the accuracy of detecting the amount of displacement by making the measurement result of the central part of the region of interest dominant.

Furthermore, the method for controlling an ultrasonic diagnostic apparatus according to the present disclosure is a method for controlling an ultrasonic diagnostic apparatus that calculates a propagation speed of a shear wave by exciting the shear wave within a subject by using an ultrasonic probe, the method including: determining a focal position of a push wave for generating a displacement within the subject, and positions of a plurality of observation points in a region of interest indicating an analysis target range within the subject; causing the ultrasonic probe to perform transmission of a push wave focusing on the focal position, and subsequent to the transmission, causing the ultrasonic probe to transmit a detection wave passing through the region of interest within the subject, and calculating amounts of displacement of tissue of the subject at the plurality of observation points on the basis of a reflected wave obtained by the ultrasonic probe in response to the transmission of the detection wave; calculating propagation speeds of the shear wave in the tissue of the subject with respect to the plurality of observation points on the basis of the amounts of displacement; evaluating values of the propagation speeds calculated to create an evaluation result; when the evaluation result does not satisfy a requirement, determining a new focal position and positions of a new plurality of observation points in which at least one of the focal position or the positions of the plurality of observation points is changed on the basis of the evaluation result, and for the new focal position and the positions of the new plurality of observation points determined, calculating the amounts of displacement, calculating the propagation speeds, and evaluating values of the propagation speeds newly calculated to create an evaluation result; and when the evaluation result satisfies the requirement, calculating a propagation speed value of the region of interest on the basis of the propagation speeds with respect to the plurality of observation points.

With such a configuration, an ultrasonic diagnostic apparatus can be implemented that can improve the reliability of the absolute value of the measurement signal value of the mechanical property by improving the accuracy of detecting the amount of displacement, in the ultrasonic elastic modulus measurement that obtains the absolute value of the mechanical property of the tissue from the narrow region of interest.

<<Supplement>>

The embodiments described above each are a preferred specific example of the present invention. Numerical values, shapes, materials, components, arrangement positions and connection forms of the components, steps, order of the steps, and the like described in the embodiments are merely examples, and are not intended to limit the present invention. In addition, among the components in the embodiments, steps not described in the independent claims that describe the highest concept of the present invention are described as arbitrary components that constitute a more preferable embodiment.

In addition, for easy understanding of the invention, the scales of the components in each of the drawings described in the above embodiments may be different from actual ones. In addition, the present invention is not limited by the description of the above embodiments, and can be changed as appropriate in a range without departing from the gist of the present invention.

Further, in the ultrasonic diagnostic apparatus, there are also members such as circuit parts and lead wires on a circuit board, but various aspects can be implemented on the basis of ordinary knowledge in the technological field for electric wiring and electric circuits, and is not directly relevant to the description of the present invention, so that the description thereof is omitted. Note that, each of the drawings illustrated above is a schematic diagram, and is not necessarily strictly illustrated.

An ultrasonic diagnostic apparatus and an ultrasonic signal processing method according to the present disclosure are useful for measuring a mechanical property of a subject using ultrasonic waves. For that reason, it is possible to improve the measurement accuracy of the mechanical property of the tissue or the substance, and has high applicability in medical diagnostic equipment, nondestructive inspection equipment, and the like.

Although embodiments of the present invention have been described and illustrated in detail, the disclosed embodiments are made for purposes of illustration and example only and not limitation. The scope of the present invention should be interpreted by terms of the appended claims.

What is claimed is:

1. An ultrasonic diagnostic apparatus that calculates a propagation speed of a shear wave by exciting the shear wave within a subject by using an ultrasonic probe, the ultrasonic diagnostic apparatus comprising a hardware processor configured to:
   determine a focal position of a push wave for generating a displacement within the subject, and positions of a plurality of observation points in a region of interest indicating an analysis target range within the subject,
   cause the ultrasonic probe to perform transmission of a push wave focusing on the focal position, and subsequent to the transmission, cause the ultrasonic probe to transmit a detection wave passing through the region of interest within the subject, and calculate amounts of displacement of tissue of the subject at the plurality of observation points on the basis of a reflected wave obtained by the ultrasonic probe in response to the transmission of the detection wave,
   calculate propagation speeds of the shear wave in the tissue of the subject with respect to the plurality of observation points on the basis of the amounts of displacement, and
   evaluate values of the propagation speeds calculated to create an evaluation result,
   wherein the hardware processor is further configured to,
   when the evaluation result does not satisfy a predetermined requirement, determine a new focal position and positions of a new plurality of observation points in which at least one of the focal position or the positions of the plurality of observation points is changed on the basis of the evaluation result, and for the new focal position and the positions of the new plurality of observation points determined, calculate the amounts of displacement, calculate the propagation speeds, and evaluate values of the propagation speeds newly calculated to create an evaluation result, and
   when the evaluation result satisfies the requirement, calculate a propagation speed value in the region of interest on the basis of the propagation speeds with respect to the plurality of observation points,
   wherein the hardware processor includes an evaluation target division selector configured to select a first division and a final division to be evaluated among divisions between adjacent observation points of the plurality of observation points, the first division being closest to the focal point of the push wave and the final division being farthest from the focal point of the push wave, wherein at least one observation point of the plurality of observation points is separate from and disposed between the first division and the final division;

an evaluation target speed obtainer configured to obtain a propagation speed corresponding to the first division and a propagation speed corresponding to the final division; and a target speed evaluator configured to determine whether the evaluation result of the propagation speed corresponding to the first division and of the propagation speed corresponding to the final division satisfy the predetermined requirement.

2. The ultrasonic diagnostic apparatus according to claim 1, wherein the target speed evaluator is configured to output an evaluation result as being appropriate when the propagation speed corresponding to the first division is less than a first threshold, and output an evaluation result as being inappropriate when the propagation speed corresponding to the first division is greater than or equal to the first threshold, and wherein the hardware processor is further configured to, when the evaluation result is output as being inappropriate, determine a new focal position and positions of a new plurality of observation points that are obtained by increasing distances between the focal position and the positions of the plurality of observation points.

3. The ultrasonic diagnostic apparatus according to claim 1, wherein the evaluation target division selector is configured to select a second division adjacent to the first division, the evaluation target speed obtainer is configured to obtain a propagation speed corresponding to the second division, the target speed evaluator is configured to output an evaluation result as being appropriate when the propagation speed corresponding to the second division is greater than or equal to the propagation speed corresponding to the first division, and output an evaluation result as being inappropriate when the propagation speed corresponding to the second division is less than the propagation speed corresponding to the first division, and wherein the hardware processor is further configured to, when the evaluation result is output as being inappropriate, determine a new focal position and positions of a new plurality of observation points that are obtained by increasing distances between the focal position and the positions of the plurality of observation points.

4. The ultrasonic diagnostic apparatus according to claim 1, wherein the evaluation target speed obtainer is configured to obtain a measurement quality value of time-series data of the amount of displacement at an observation point corresponding to the final division, the target speed evaluator is configured to output an evaluation result as being appropriate when the measurement quality value is greater than or equal to a second threshold, and output an evaluation result as being inappropriate when the measurement quality value is less than the second threshold, and wherein the hardware processor is further configured to, when the evaluation result is output as being inappropriate, determine a new focal position and positions of a new plurality of observation points that are obtained by decreasing distances between the focal position and the positions of the plurality of observation points.

5. The ultrasonic diagnostic apparatus according to claim 4, wherein the measurement quality value is a parameter based on one or more elements selected from a variance, a signal level, and a noise level of the amounts of displacement or acoustic ray signals on which the amounts of displacement depend.

6. The ultrasonic diagnostic apparatus according to claim 1, wherein in a case where the target speed evaluator outputs an evaluation result as being inappropriate, and in a case where the plurality of observation points on which the evaluation target division depends is obtained by determination of the new focal position and the positions of the new plurality of observation points by the hardware processor having already performed a first change for distances between the focal position and the positions of the plurality of observation points, and in a case where, on the basis of the evaluation result as being inappropriate, the hardware processor is configured to determine a further new focal position and positions of a further new plurality of observation points by performing a second change opposite to the first change for the distances between focal position and the positions of the plurality of observation points, the target speed evaluator is configured to output an evaluation result as being appropriate regarding the evaluation target division, and the hardware processor is further configured to calculate a propagation speed value of the region of interest by multiplying the propagation speeds with respect to the plurality of observation points by a weight sequence in which a weight of a central part of the region of interest along a propagation direction is increased.

7. A method for controlling an ultrasonic diagnostic apparatus that calculates a propagation speed of a shear wave by exciting the shear wave within a subject by using an ultrasonic probe, the ultrasonic diagnostic apparatus including a hardware processor performing the method comprising:

determining a focal position of a push wave for generating a displacement within the subject, and positions of a plurality of observation points in a region of interest indicating an analysis target range within the subject;

causing the ultrasonic probe to perform transmission of a push wave focusing on the focal position, and subsequent to the transmission, causing the ultrasonic probe to transmit a detection wave passing through the region of interest within the subject, and calculating amounts of displacement of tissue of the subject at the plurality of observation points on the basis of a reflected wave obtained by the ultrasonic probe in response to the transmission of the detection wave;

calculating propagation speeds of the shear wave in the tissue of the subject with respect to the plurality of observation points on the basis of the amounts of displacement;

evaluating values of the propagation speeds calculated to create an evaluation result;

when the evaluation result does not satisfy a requirement, determining a new focal position and positions of a new plurality of observation points in which at least one of the focal position or the positions of the plurality of observation points is changed on the basis of the evaluation result, and for the new focal position and the positions of the new plurality of observation points determined, calculating the amounts of displacement, calculating the propagation speeds, and evaluating values of the propagation speeds newly calculated to create an evaluation result; and when the evaluation result satisfies the requirement, calculating a propagation speed value of the region of interest on the basis of the propagation speeds with respect to the plurality of observation points, the step of calculating propagation speeds includes selecting a first division and a final division to be evaluated among divisions between adjacent observation points, the first division being closest to the focal point of the push wave and the final division being farthest from the focal point of the push wave, wherein at least one observation point of the adjacent observation point is separate from and disposed between the first division and the final division, and calculating a propagation speed corresponding to the first division and a propagation speed corresponding to the final division, and the step of evaluating includes determining whether the evaluation result, result of the propagation speed corresponding to the first division and of the propagation speed corresponding to the final division satisfy the predetermined requirement.

8. The ultrasonic diagnostic apparatus according to claim 1, wherein
the hardware processor is configured to, when the evaluation result does not satisfy a predetermined requirement, determine the new focal position and positions of a new plurality of observation points in which at least one of the focal position or the positions of the plurality of observation points is changed in a direction orthogonal to a depth direction of the push wave.

9. The ultrasonic diagnostic apparatus according to claim 1, wherein
the detection wave is a plane wave having a length that larger than a width of the region of interest and centered around the focal position of the push wave, whereby acoustic signals are generated for the plurality of observation points in an entirety of the region of interest by one transmission and reception of the detection wave.

10. The ultrasonic diagnostic apparatus according to claim 1, wherein
the target speed evaluator is configured to determine whether the first division is in an initial distortion region based on the propagation speed corresponding to the first division, the initial distortion region being an area around the push wave focal point in which a physical distortion is induced by the push wave.

11. The ultrasonic diagnostic apparatus according to claim 1, wherein
the hardware processor determines the new focal position and the positions of the new plurality of observation points based on the evaluation result of the propagation speed corresponding to the first division and of the propagation speed corresponding to the final division.

12. The ultrasonic diagnostic apparatus according to claim 1, wherein
the first division includes divisions between adjacent observation points of the plurality of observation points that are closest to the focal point of the push wave.

* * * * *